US012564420B2

(12) United States Patent
Dib et al.

(10) Patent No.: US 12,564,420 B2
(45) Date of Patent: *Mar. 3, 2026

(54) NEEDLE GUIDANCE SYSTEM

(71) Applicant: Accurate Access, LLC, Paradise Valley, AZ (US)

(72) Inventors: Nabil Dib, Paradise Valley, AZ (US); David Skodje, Paradise Valley, AZ (US); Robert Kohler, Paradise Valley, AZ (US); Brian Beaubien, Paradise Valley, AZ (US)

(73) Assignee: Accurate Access, LLC, Paradise Valley, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/984,429

(22) Filed: Dec. 17, 2024

(65) Prior Publication Data

US 2025/0114120 A1 Apr. 10, 2025

Related U.S. Application Data

(63) Continuation of application No. 18/048,780, filed on Oct. 21, 2022, now Pat. No. 12,201,319.

(51) Int. Cl.
*A61B 17/34* (2006.01)

(52) U.S. Cl.
CPC ... *A61B 17/3403* (2013.01); *A61B 2017/3411* (2013.01); *A61B 2017/3413* (2013.01)

(58) Field of Classification Search
CPC ........ A61B 17/3403; A61B 2017/3411; A61B 2017/3413; A61B 2034/2065;

(Continued)

(56) References Cited

U.S. PATENT DOCUMENTS 5,758,650 A 6/1998 Miller et al.
6,361,499 B1 3/2002 Bates et al.
(Continued)

FOREIGN PATENT DOCUMENTS

EP 4052668 A1 9/2022
WO WO2015037418 A1 3/2015

OTHER PUBLICATIONS

WIPO, U.S. International Search Authority, International Search Report and Written Opinion mailed Feb. 14, 2024 in International Patent Application No. PCT/US2023/075570, 9 pages.

*Primary Examiner* — Pascal M Bui Pho
*Assistant Examiner* — Michael Yiming Fang
(74) *Attorney, Agent, or Firm* — Inskeep IP Group, Inc.

(57) ABSTRACT

A guidance system for guiding an intervention device such as a needle to a target location such as a vessel while remaining within a field of view of an imaging device such as an ultrasound. The guidance system may include an attachment mechanism for removable attachment to a specific ultrasound probe or which is adaptable to multiple different probes. A guidance mechanism may extend outwardly from the attachment mechanism for guiding the angle and depth of the intervention device. The guidance mechanism may include a plurality of openings through which the intervention device may be selectively inserted, with each opening being configured for a different angle and/or depth. Alternatively, the guidance mechanism may include a single opening that is adjustable along an arcuate path. A release mechanism may be included to allow the intervention device to be safely removed from the guidance mechanism without undue movement of the intervention device.

20 Claims, 38 Drawing Sheets

(58) Field of Classification Search
  CPC ............ A61B 2090/378; A61B 8/0841; A61B 90/361; A61B 90/50; A61B 10/0233; A61B 2017/00283; A61B 90/11
  See application file for complete search history.

(56) References Cited

U.S. PATENT DOCUMENTS

| | | | |
|---|---|---|---|
| 8,073,529 | B2 | 12/2011 | Cermak et al. |
| 8,137,281 | B2 | 3/2012 | Huang et al. |
| 9,724,070 | B2 | 8/2017 | Boezaart et al. |
| 9,861,739 | B2 | 1/2018 | Sheldon et al. |
| 9,974,516 | B2 | 5/2018 | Orome et al. |
| 10,507,038 | B2 | 12/2019 | Cermak |
| 10,555,719 | B2 | 2/2020 | Tegels |
| 11,103,210 | B2 | 8/2021 | Von Allmen |
| 11,382,655 | B2 | 7/2022 | Bouazza-Marouf et al. |
| 12,201,319 | B2 * | 1/2025 | Dib ...................... A61B 8/0841 |
| 2007/0276253 | A1 | 11/2007 | Park et al. |
| 2010/0041990 | A1 | 2/2010 | Schlitt et al. |
| 2011/0313293 | A1 * | 12/2011 | Lindekugel ............ A61B 10/00 600/459 |
| 2012/0330159 | A1 | 12/2012 | Orome et al. |
| 2013/0245452 | A1 | 9/2013 | Gorzitze |
| 2014/0200445 | A1 * | 7/2014 | Boezaart .............. A61B 8/4209 600/461 |
| 2014/0343406 | A1 | 11/2014 | Damjanovic |
| 2016/0128719 | A1 | 5/2016 | Cermak |
| 2018/0280053 | A1 | 10/2018 | Coker et al. |
| 2019/0059854 | A1 | 2/2019 | Radt et al. |
| 2019/0159753 | A1 | 5/2019 | Hsu et al. |
| 2019/0209120 | A1 | 7/2019 | Gorzitze |
| 2019/0282203 | A1 | 9/2019 | Naumann et al. |
| 2019/0282262 | A1 * | 9/2019 | Bouazza-Marouf ......................... A61B 8/4455 |
| 2020/0077993 | A1 | 3/2020 | Yap et al. |
| 2020/0121278 | A1 | 4/2020 | Hagy et al. |
| 2021/0045711 | A1 | 2/2021 | Brattain et al. |
| 2022/0202444 | A1 | 6/2022 | Allaway |

* cited by examiner

170

170A

NEEDLE GUIDANCE SYSTEM

RELATED APPLICATIONS

This application is a continuation of and claims priority to U.S. patent application Ser. No. 18/048,780 filed Oct. 21, 2022 entitled Needle Guidance System, which is hereby incorporated herein by reference in its entirety.

BACKGROUND OF THE INVENTION

A wide range of medical procedures may require accurate needle puncture to access various locations within a patient's body for treatment and/or diagnosis. For example, accurate needle puncture may be required to perform vascular access, such as femoral and subclavian vessel access or tissue biopsy.

Various complications can arise if the needle is not accurately routed and placed in the desired target location. Such procedures are typically performed by a trained medical professional and, without guidance, may require multiple attempts to reach the target location. Failure to reach the target location on the first attempt can result in procedural delays, patient discomfort, and/or various medical complications.

While ultrasound imaging may be utilized to increase accuracy during such needle puncture procedures, it may be difficult to maintain needle positioning within the field of view of the ultrasound (e.g., within the ultrasound beam) to maintain clear visualization of the needle as it traverses through the patient towards the target location. In many cases, the ultrasound field of view may be very narrow (e.g., about 1 mm) which can make it very challenging to maintain the needle's alignment within the field of view during puncture.

SUMMARY OF THE INVENTION

A guidance system is described for guiding an intervention device such as a needle to a target location such as a vessel while remaining within a field of view of an imaging device such as an ultrasound.

One example embodiment may include an attachment mechanism for removable attachment to an imaging device, such as an ultrasound probe.

One example embodiment may include a guidance mechanism for guiding the intervention device along an optimal angle to an optimal depth while remaining within the field of view of the imaging device.

In an example embodiment, the guidance mechanism may be fixed in place.

In another example embodiment, the guidance mechanism may be movable along an arcuate path.

In an example embodiment, the guidance mechanism may include a plurality of openings, each extending at a different angle through the guidance mechanism, through which the intervention device may be removably inserted to be guided to the target location at a desired depth while remaining within the field of view of the intervention device.

In another example embodiment, the guidance mechanism may include a single opening, with the guidance mechanism itself being movable along the arcuate path between different angles to accommodate different depths.

In an example embodiment, the guidance mechanism may include visual, auditory, and/or tactile feedback to identify different angles and/or depths.

One example embodiment of such visual feedback may include a plurality of indicia, such as markings or grooves, which represent different angles and/or depths.

In an example embodiment, the guidance system may include a release mechanism which allows the intervention device to be safely removed from the guidance mechanism after it has reached the target location without movement of the intervention device.

In one example embodiment, the release mechanism may comprise a hinged member which may be latched shut to hold the intervention device and pivotably opened to release the intervention device.

In another example embodiment, the release mechanism may comprise a magnetic element which magnetically engages with the intervention device while in use but allows release of the intervention device upon reaching the target location. The magnetic element may assist in orientation of the intervention device.

In another example embodiment, the release mechanism may comprise one or more resilient flaps which adjust outwardly to allow the intervention device to be released before resiliently returning to their original position.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION

Figure 1:
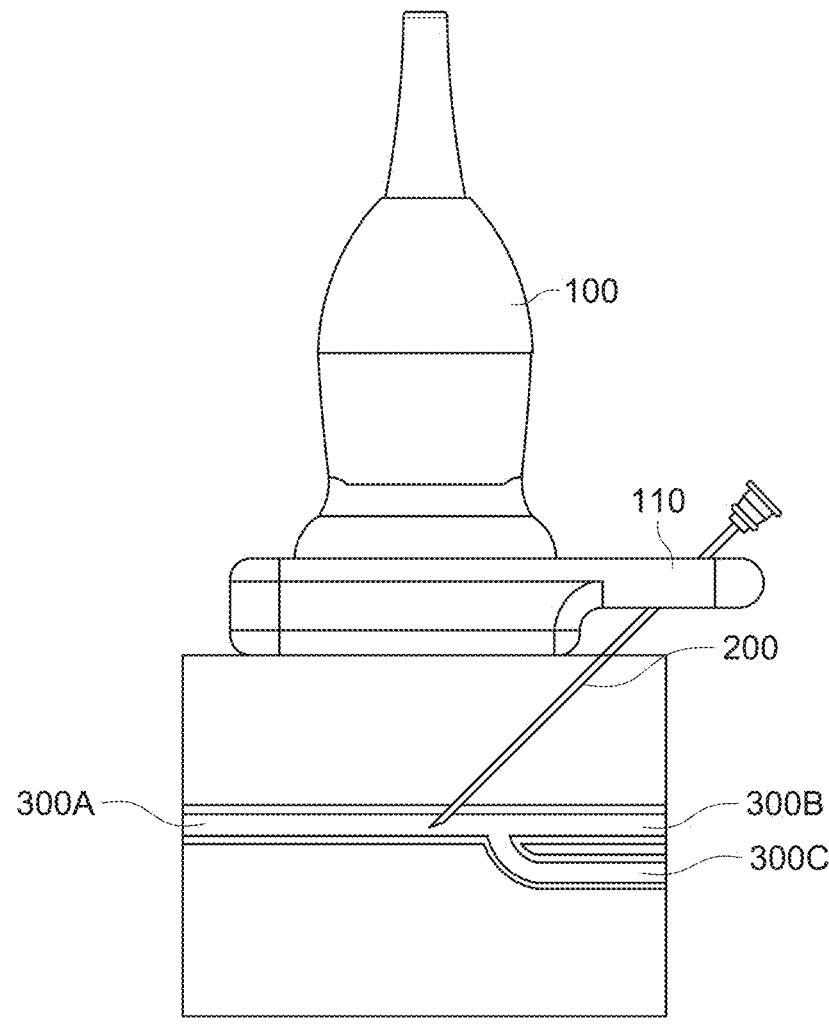
FIG. 1 is a front view of a needle guidance system in use according to an example embodiment.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Described herein are various example embodiments of a needle guidance system which may be utilized to guide the positioning and angle of an intervention device such that the intervention device is within the field of view of an imaging device. Generally, the methods and systems described and/or shown herein may be used to guide any intervention device having an elongated body such that the intervention device is maintained within the view of any imaging device while the intervention device is delivered to a target location. The methods and systems described and/or shown herein may be utilized with human or animal patients and for various purposes, including but not limited to vascular access, tissue biopsy, and the like.

As a non-limiting example, the intervention device may comprise a needle, such as a syringe, and the imaging device may comprise an ultrasound. A guidance mechanism may be utilized to guide the intervention device while it is routed to a target location, such as a vessel. The guidance mechanism may be fixedly attached, removably attached, or integrated with the imaging device.

Generally, the guidance mechanism may be positioned at or near a distal end of the imaging device. For example, the guidance mechanism may be positioned at or near a probe of the imaging device. However, in some embodiments, it should be appreciated that the guidance mechanism may be positioned further from the probe of the imaging device than shown in the figures, such as near the handle, so long as the angles are adjusted accordingly.

In embodiments in which the guidance mechanism is removably attached to the imaging device, an attachment mechanism may be removably attached in various manners to various positions on the body of the imaging device, such as at or near its distal end. The attachment mechanism may be sized to fit a specific imaging device, in which case multiple attachment mechanisms may be designed for different imaging devices. Alternatively, the attachment mechanism may function as an adapter to fit multiple different imaging device, such as different types of imaging devices or imaging devices from different manufacturers.

The guidance mechanism may be utilized to guide an intervention device so as to remain in the field of view of the imaging device both during delivery to a target location and upon reaching the target location. For example, the guidance mechanism may be utilized to guide a needle to puncture a vessel such that the needle remains in the field of view of an ultrasound both while the needle is being advanced and at the point of insertion into the vessel.

In some example embodiments, the guidance mechanism may include multiple openings, slots, notches, grooves, or the like through which the intervention device may be selectively routed at an optimal angle so as to remain within the field of view of the imaging device during delivery and upon arrival at the target location.

Figure 17:
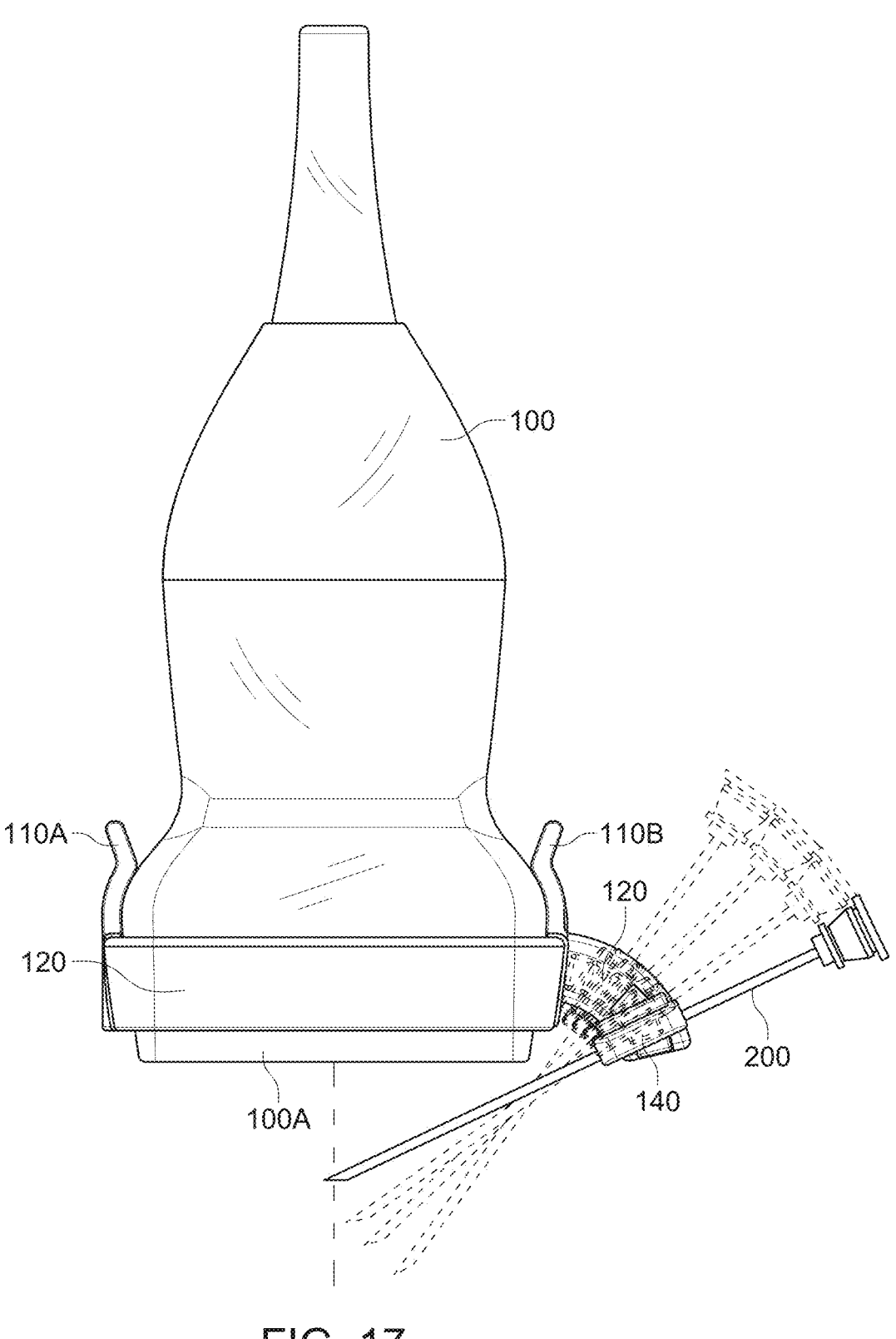
FIG. 17 is a front view of a needle guidance system illustrating multiple needle positions according to an example embodiment.

In some example embodiments, the guidance mechanism may include a single opening, slot, notch, groove, or the like that is movable along an arcuate path. FIGS. 3-9 and 16-23C illustrate example embodiments of a guidance mechanism having a single opening, slot, notch, groove, or the like that is movable along an arcuate path for guiding the intervention device at a desired angle to a desired depth while remaining within the field of view of the imaging device. In such embodiments, adjustment of the guidance mechanism may function to pivot the positioning of the intervention device about a single pivot point (e.g., the intersection between the illustrated intervention devices shown in FIGS. 5 and 17).

In other example embodiments, the guidance mechanism may include multiple (e.g., two or more) openings, slots, notches, grooves, or the like that may be individually selected to guide the intervention device at a desired angle to a desired depth while remaining within the field of view of the imaging device. FIGS. 10-15 illustrate such an example embodiment.

Figure 19A:
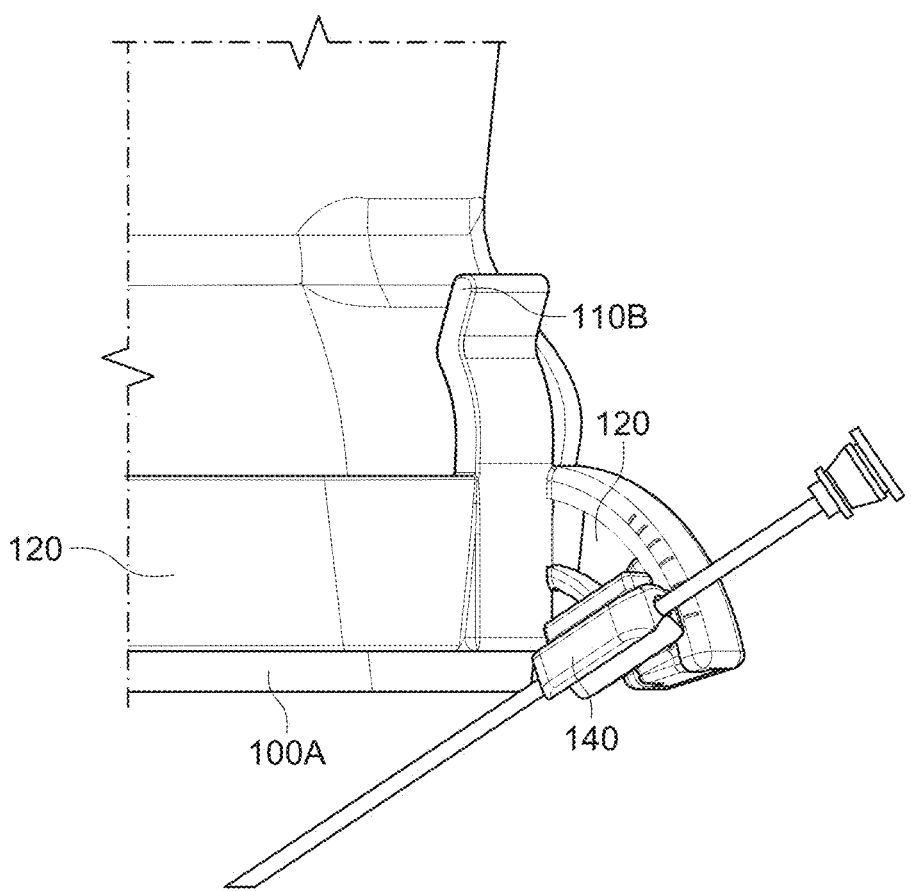
FIG. 19A is a perspective view of a needle guidance system illustrating a needle release mechanism according to an example embodiment.
Figure 19B:
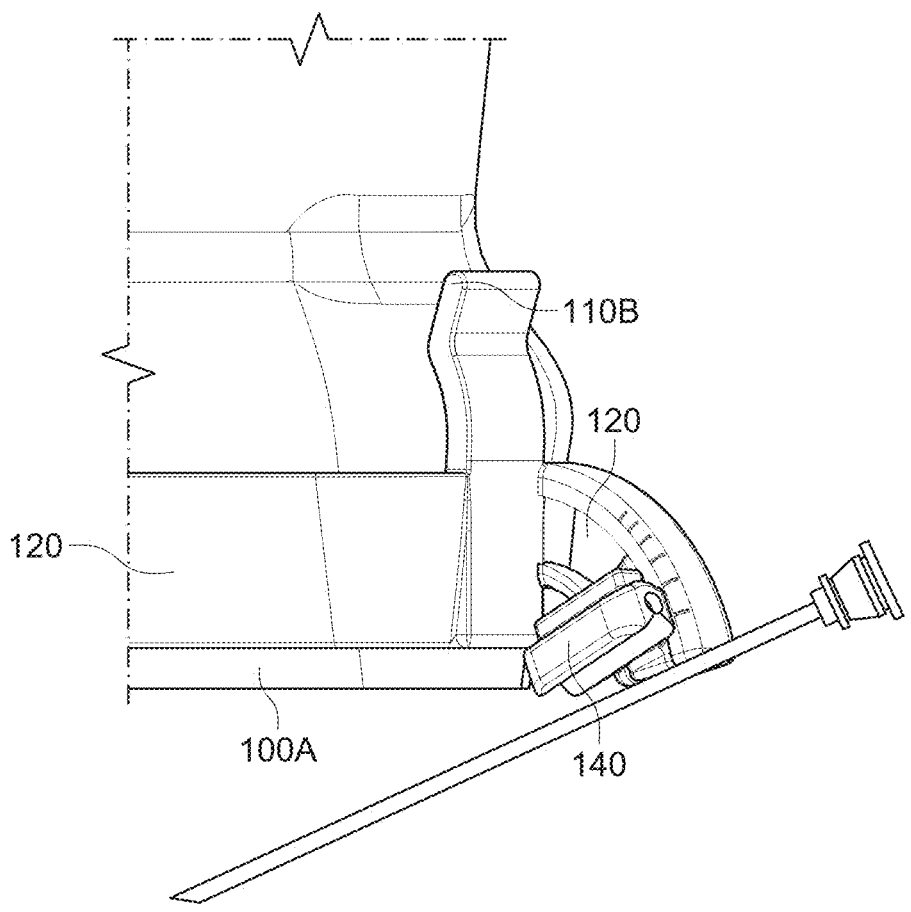
FIG. 19B is a perspective view of a needle guidance system illustrating a needle release mechanism according to an example embodiment.
Figure 20A:
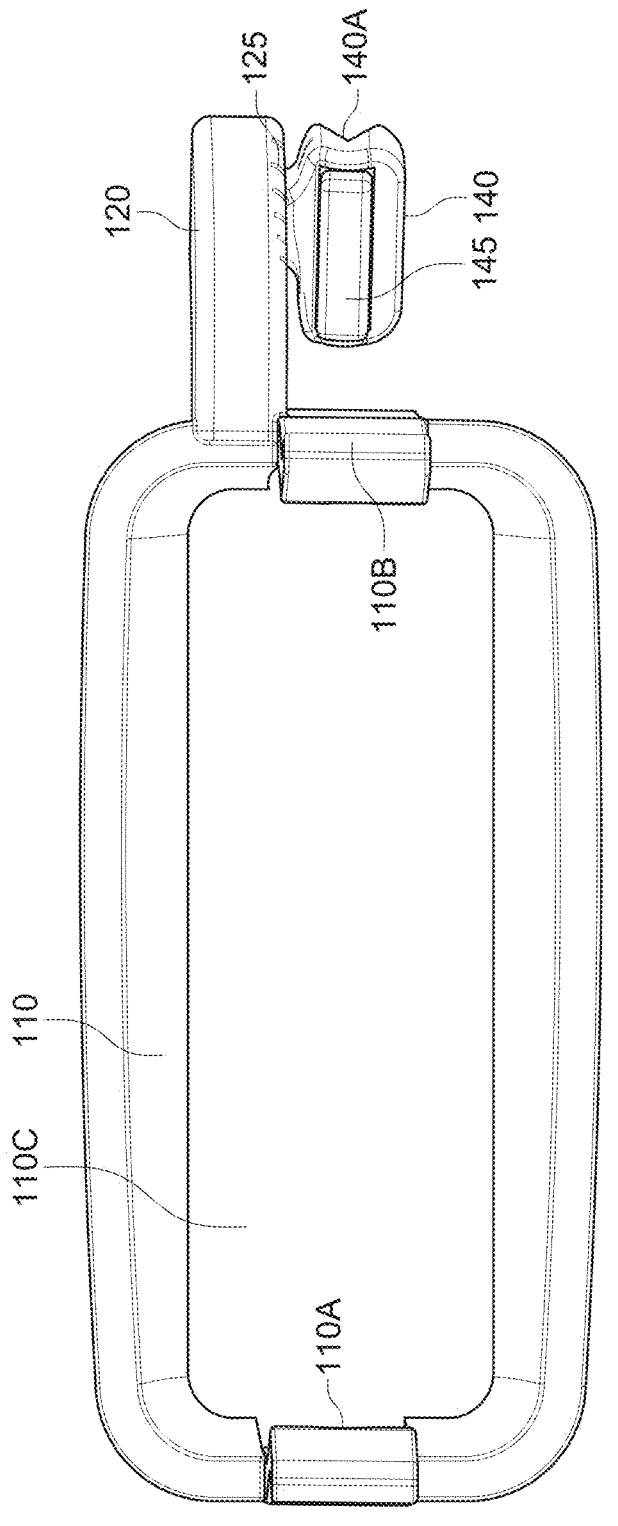
FIG. 20A is a top view of a needle guidance system according to an example embodiment.
Figure 20B:
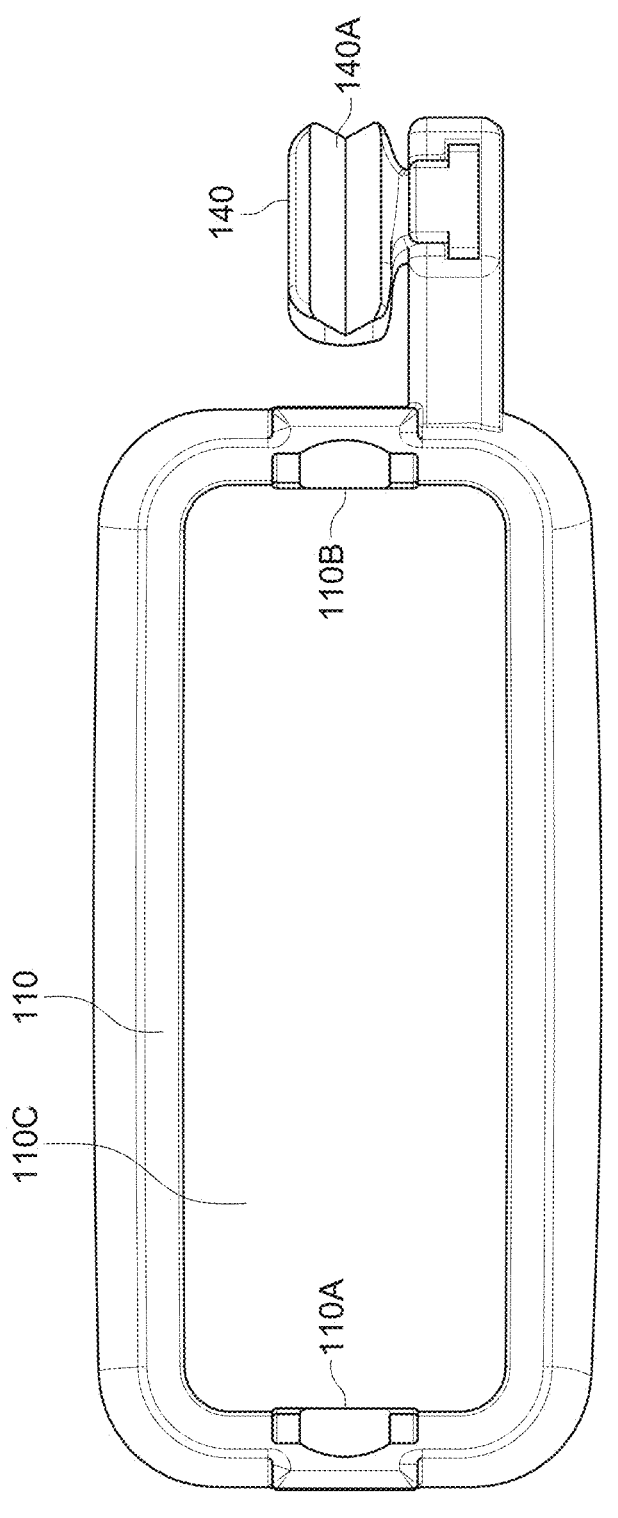
FIG. 20B is a bottom view of a needle guidance system according to an example embodiment.

In some example embodiments, the guidance mechanism may include a release mechanism such that the intervention device may be safely and efficiently removed from the guidance mechanism without moving the intervention device out of its position and angle. FIGS. 12A-15 illustrate an embodiment in which the guidance mechanism may be swung open, such as by a hinge, to allow the guidance mechanism to be removed from around the intervention device without any movement of the intervention device. FIGS. 24A-24B and 26A-26B illustrate example embodiments in which the guidance mechanism may be pivotally adjusted. FIGS. 19A-19B illustrate example embodiments in which the guidance mechanism includes a release slot such that the guidance mechanism may be pulled away from the intervention device without any movement of the intervention device.

In embodiments in which the guidance mechanism is adjustable along an arcuate path such as shown in FIGS. 3-9 and 16-23C, the arcuate path may have preset intervals which may be indicated by various types of feedback, such as visual, auditory, and/or haptic feedback. For example, the guidance mechanism may click upon reaching different preset angular intervals. As a further example, indicia such as markings may indicate different present angular intervals. However, in some embodiments, the arcuate path may not have preset intervals (e.g., no feedback of any kind may be provided).

FIGS. 10-15 illustrate an example embodiment of a guidance mechanism 150 which utilizes multiple, selectable openings for guiding the positioning and angle of an intervention device such as a needle towards a target location while remaining within the field of view of an imaging device such as an ultrasound probe.

The illustrated example embodiment shown in FIGS. 1-4B may utilize four openings that enable vascular access from 1.5 cm to 4.0 cm deep. In such an embodiment, the imaging device 100 may be positioned on the patient with a vessel aligned within its field view. For a given opening, a standard 7 cm length needle can be driven to a range of depths while remaining within the field of view of the imaging device 100. The angle and location of the openings may enable continuous access to the full range of depths (e.g., 1.5 cm to 4.0 cm or more depth).

Generally, the needle guidance system may provide a scale to indicate an appropriate depth at which an intervention device will cross a centerline of an imaging device 100, measured from the bottom face of the probe of the imaging device. The arc center-point and radius may be selected to meet several design requirements. As a non-limiting example, the needle length from the guidance mechanism to the centerline of the probe may be less than or equal to 67 mm to enable function with a standard 7 cm needle. As another non-limiting example, the needle length from the guidance mechanism to the centerline of the probe may be less than or equal to 87 mm to enable function with a 9 cm needle. Various other values may be utilized in different embodiments to accommodate different needle types.

The gap between the needle path centerline and the probe 100A will preferably exceed some minimal amount to ensure clearance between the needle and the probe 100A (or a sterile cover thereof) to prevent puncture of the sterile cover when used. For a standard 18-gauge needle having a diameter of approximately 1.3 mm, the gap will preferably be between 1-2 mm at a minimum. The needle angle relative to the bottom face of the imaging device probe will preferably be below a maximum value to enable ease of target location access. The limits of the arc will preferably leave sufficient space for the guidance mechanism when the needle is at the maximum and minimum depths. The guidance mechanism will preferably be long enough to stabilize the needle in its opening, but without interfering with the patient's skin at one limit, or the probe at the other limit.

It should be appreciated that the angle and depth measurements utilized to retain the intervention device within the field of view of the imaging device during delivery to a target location may be calculated in various manners. As a first example, the Pythagorean theorem ($a^2+b^2=c^2$) may be utilized, with a representing the sum of the distance of the puncture site from the surface of the body (as measured by an imaging device) and the distance from the surface of the body to the needle holder, b representing the distance from the needle holder to the needle location on the needle holder, and c representing the distance that the needle needs to travel from the needle location on the needle holder to the puncture site. As a second example, the formula $$\operatorname{Sin}\Theta = \frac{b}{c} = n$$

may be utilized to perform the same functionality. However, various other methods may be utilized to perform the necessary calculations to determine optimal angle and depth measurements to ensure that the needle remains in the field of view of the imaging device during delivery and arrival at the target location (puncture site).

Specific example embodiments are described further below. However, it should be understood that any of the features from any of the embodiments can be mixed and matched with each other in any combination. Hence, the present invention should not be restricted to only these embodiments, but any broader combination thereof.

FIG. 1 illustrates an example embodiment of an imaging device 100 being positioned on the skin of a patient. An attachment mechanism 110 may be utilized to removably attach a guidance mechanism 120 to the imaging device 100, with the guidance mechanism 120 being utilized to guide an intervention device 200 to puncture a vessel while remaining within a field of view of the imaging device 100.

FIG. 1 illustrates an example embodiment in which the intervention device 200 is puncturing a common femoral artery 300A, near a bifurcation of the superficial femoral artery 300B and the internal femoral artery 300C. It should be appreciated that FIG. 1 merely illustrates one example of usage. The systems and methods shown and/or described herein may be utilized in connection with delivering an intervention device 100 to a wide range of different vessels or other internal areas of a body. Thus, the scope should not be construed as limited to the particular positioning of the imaging device 100 illustrated in the example embodiment of FIG. 1.

Figure 2A:
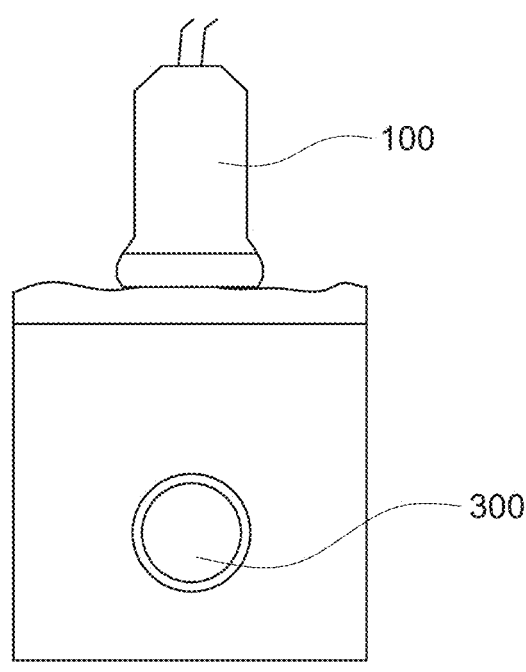
FIG. 2A is a side view illustrating a needle guidance system utilizing short access guidance according to an example embodiment.
Figure 2B:
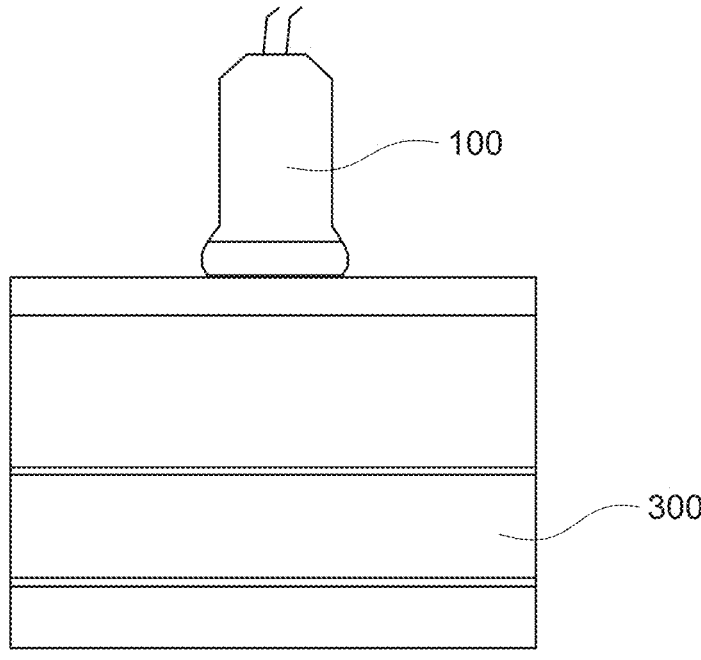
FIG. 2B is a front view illustrating a needle guidance system utilizing long access guidance according to an example embodiment.

It should be appreciated that the systems and methods shown and/or described herein may be utilized for both short access guidance and long access guidance, depending on the positioning of the imaging device 100. FIG. 2A illustrates positioning of an imaging device 100 for short access guidance of a vessel 300 according to an example embodiment. FIG. 2B illustrates positioning of an imaging device 100 for long access guidance of a vessel 300 according to an example embodiment.

Figure 3:
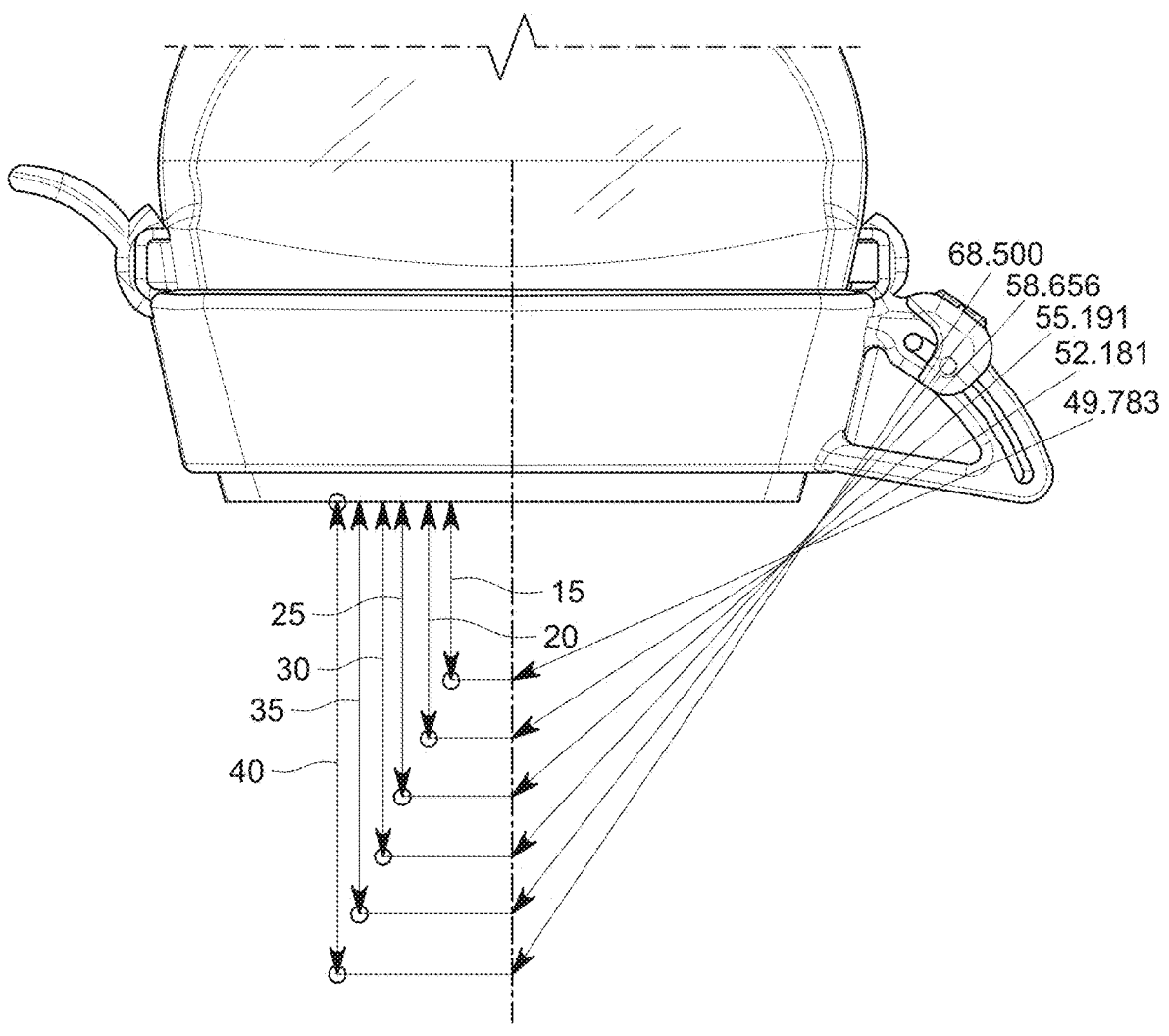
FIG. 3 is a front view illustrating exemplary depth and angle measurements of a needle guidance system according to an example embodiment.

FIG. 3 illustrates example depth settings for an example embodiment in which an attachment mechanism 110 is utilized to attach a guidance mechanism 120 to an imaging device 100. In the example embodiment shown in FIG. 3, it can be seen that six needle depth settings are shown. It should be appreciated that the systems and methods shown and/or described herein may support more or less than six needle depth settings in some embodiments. It should also be appreciated that even more depth settings may be achievable by positioning the intervention device 200 between marked depth settings.

Continuing to reference FIG. 3, it can be seen that the depths are illustrated as ranging from 15 mm to 40 mm below the imaging device 100 surface and needle lengths ranging from 49.8 mm to 66.5 mm. It should be appreciated that such settings, including depth and length settings, may vary in different embodiments and thus should not be construed as limited by the example embodiment shown in the diagram of FIG. 3.

As shown in FIGS. 4-5, 10-11B, 16-17, 22-23C, and 28A-28B, an attachment mechanism 110 may be removably attached to an imaging device 100. The attachment mechanism 110 may include an opening 110C through which the imaging device 100, such as a probe 100A of the imaging device 100, may be removably inserted. The imaging device 100 may be frictionally engaged within the opening 110C such that the attachment mechanism 110 is secured to the imaging device 100.

In some embodiments, the attachment mechanism 110 may include one or more tabs 110A, 110B which releasably engage with one or more outer edges of the imaging device 100. The example embodiment of FIG. 1 illustrates an attachment mechanism 110 having a pair of such tabs 110A, 110B-a first tab 110A for engaging with a first side of the imaging device 100 and a second tab 110B for engaging with a second side of the imaging device 100. When the imaging device 100 is inserted through the opening 110C of the attachment mechanism 110, the tabs 110A, 110B may "snap" into place.

Figure 4:
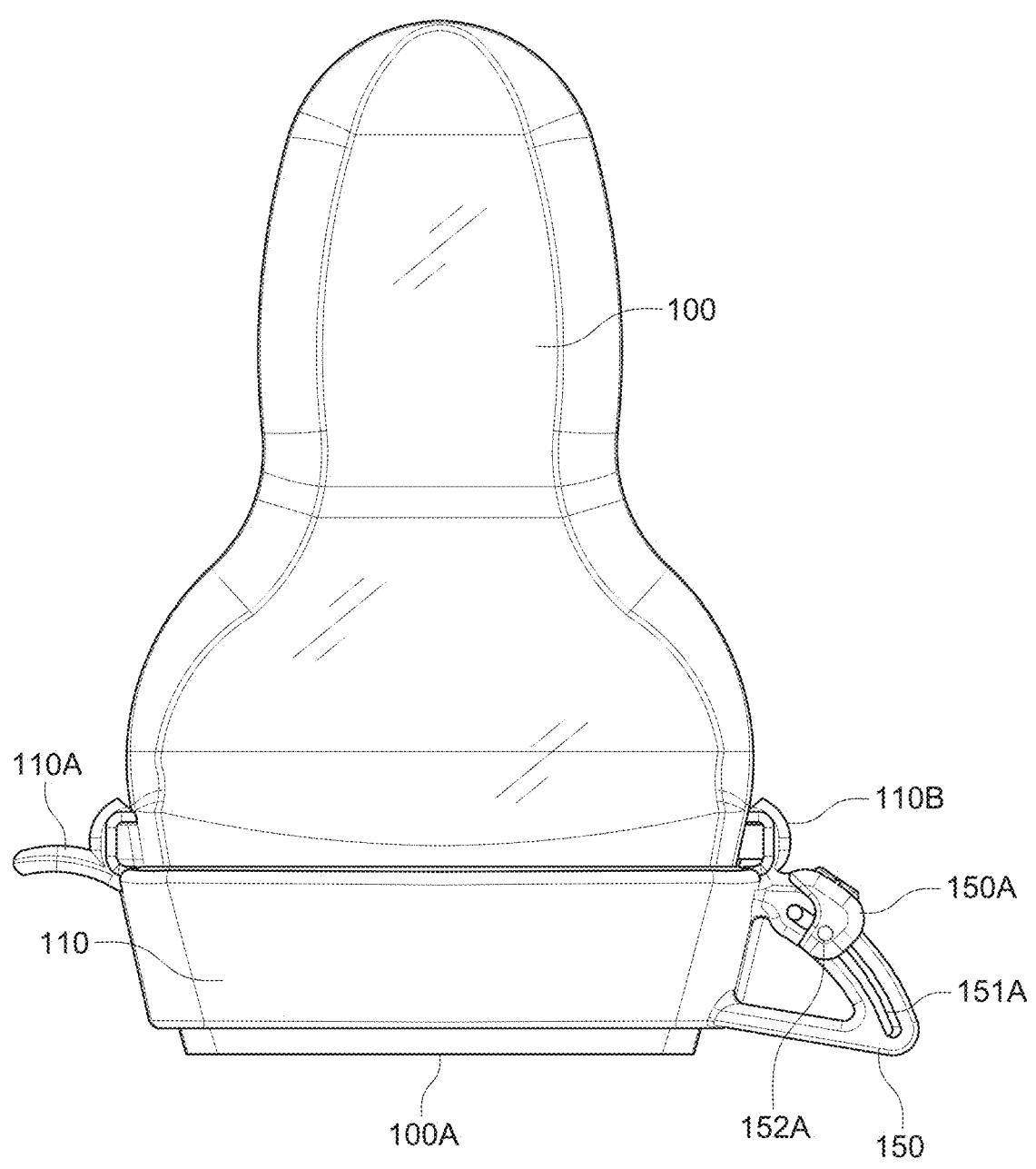
FIG. 4 is a front view of a needle guidance system according to an example embodiment.
Figure 10:
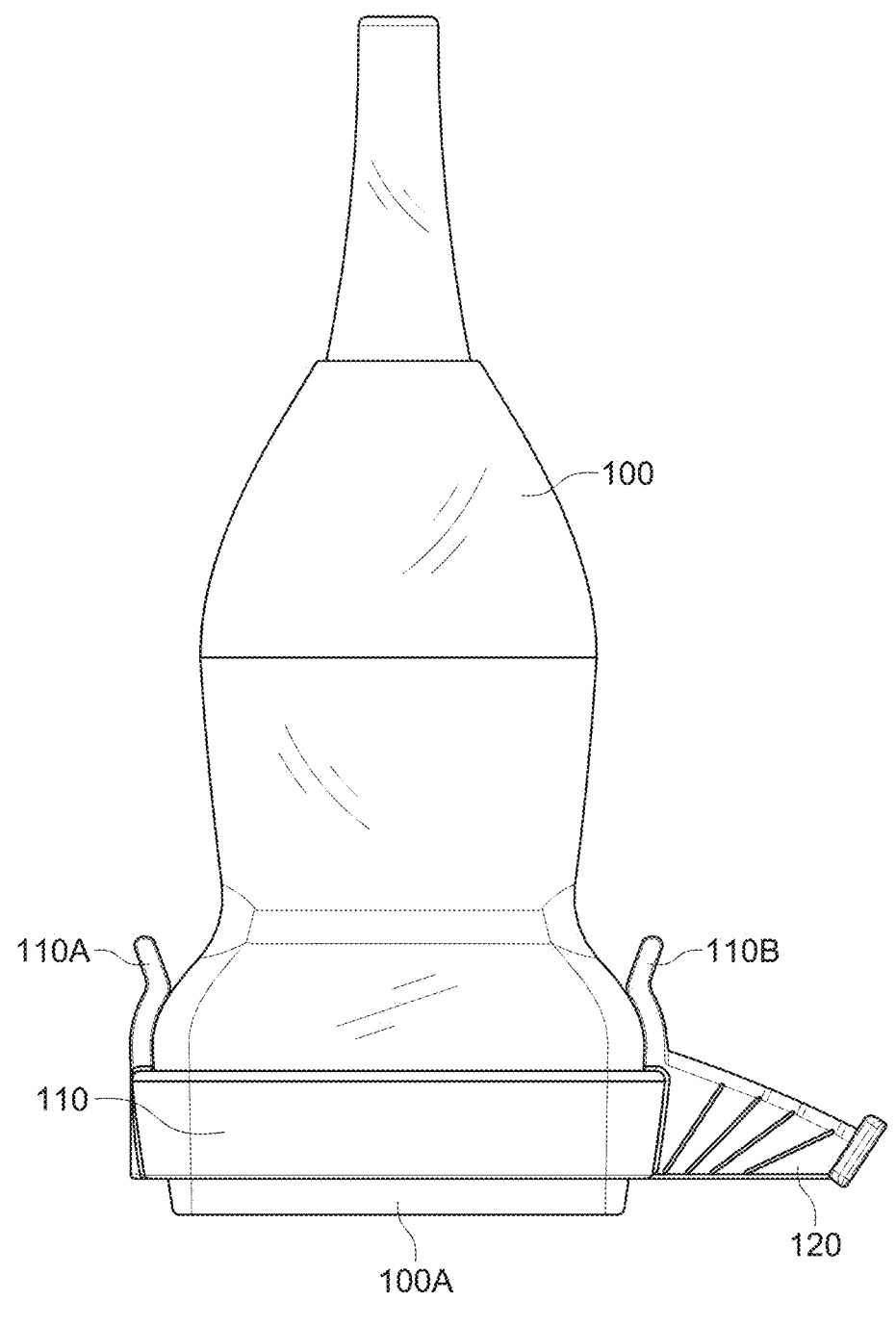
FIG. 10 is a front view of a needle guidance system according to an example embodiment.

As shown in FIGS. 4 and 10, each tab 110A, 110B may have a curved inner edge which closely matches the contour of a curved outer edge of the imaging device 100. Each tab 110A, 110B may also include a release, such as a handle or the like, which may be adjusted outwardly away from the imaging device 100 to release the tabs 110A, 110B from engagement such that the attachment mechanism 110 may be slid off the end of the imaging device 100. In this manner, the attachment mechanism 110 may be removed from the imaging device 100 when not needed and stored for future use in embodiments in which the guidance mechanism 150 is removably attached to, rather than fixedly attached to or integrally formed with, the imaging device 100.

Figure 11A:
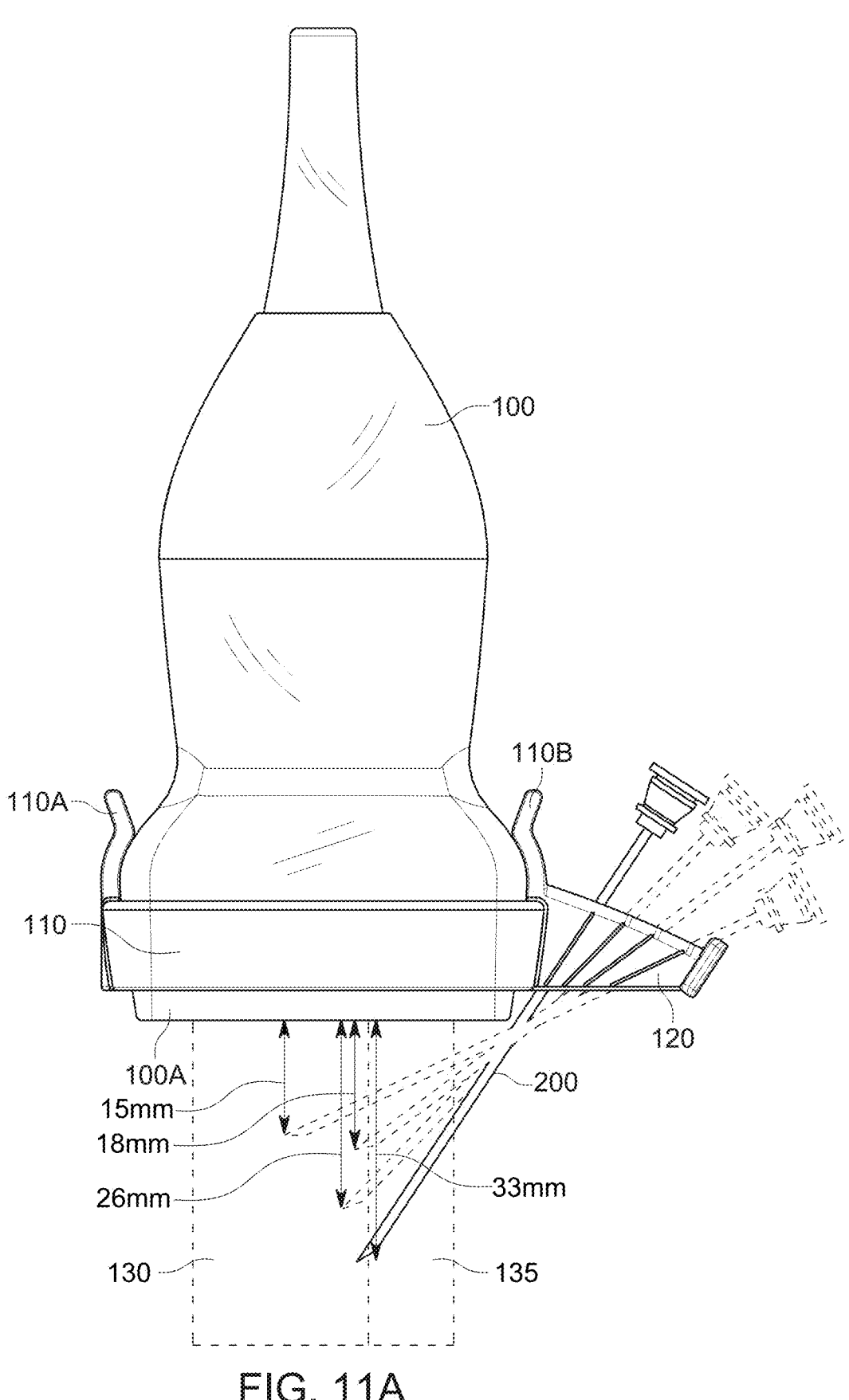
FIG. 11A is a front view of a needle guidance system illustrating multiple needle positions at a minimum depth according to an example embodiment.
Figure 11B:
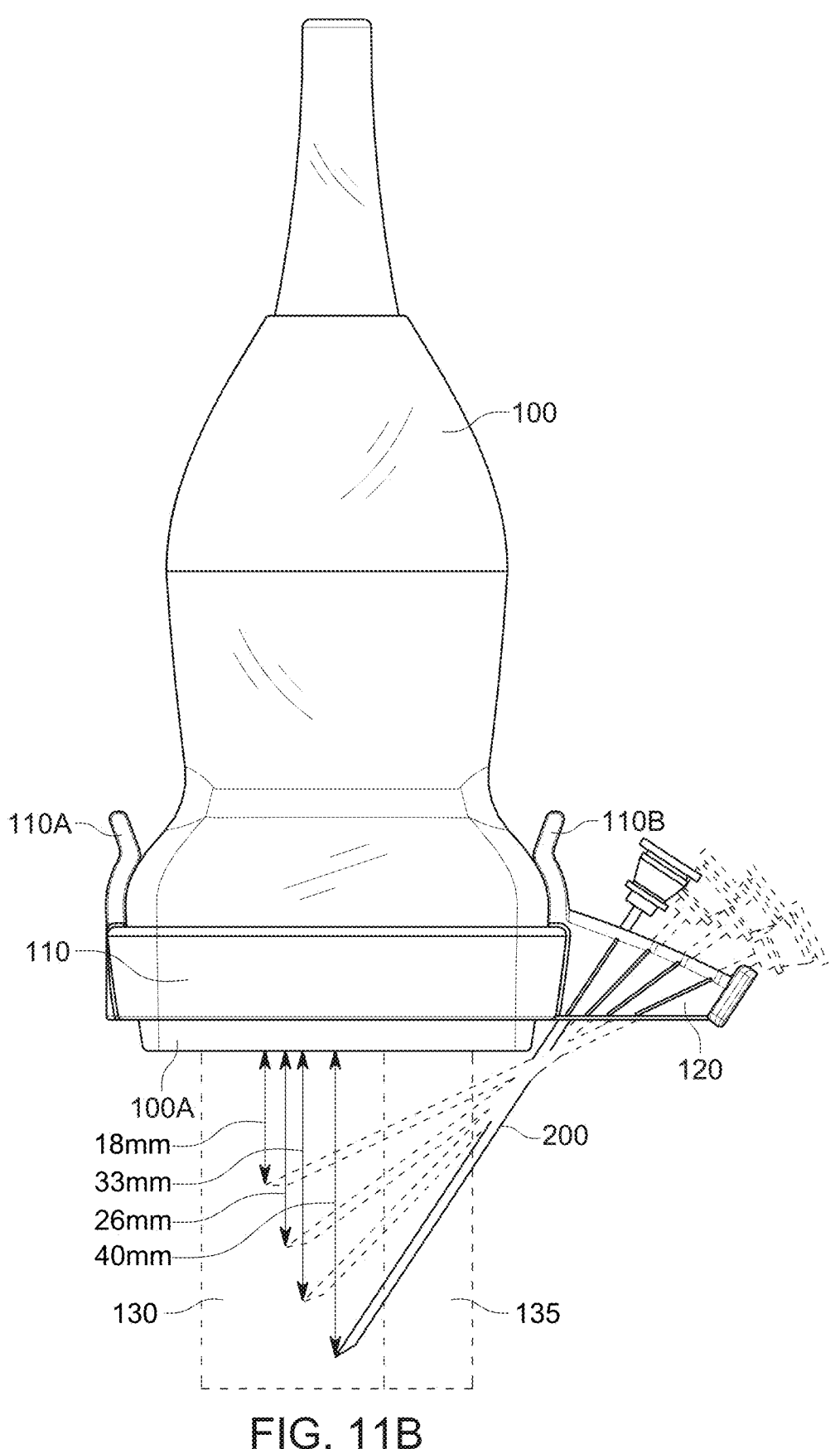
FIG. 11B is a front view of a needle guidance system illustrating multiple needle positions at a maximum depth according to an example embodiment.

FIGS. 11A-11B illustrate the attachment mechanism 110 secured to an imaging device 100, with intervention devices 200 being illustrated within the various guidance openings 120A, 120B, 120C, 120D of the guidance mechanism 120. FIG. 11A illustrates the intervention devices 200 inserted to a minimum specified depth and FIG. 11B illustrates the intervention devices 200 inserted to a maximum specified depth while remaining within the field of view of the imaging device 100. Although FIGS. 11A-11B illustrate such concepts in relation to an example embodiment of a guidance mechanism 120 having fixed openings, it should be appreciated that such concepts equally apply to any of the other embodiments shown and/or described herein.

Continuing to reference FIGS. 11A-11B, it can be seen that the imaging device's 100 field of view may be divided into two regions-a puncture zone 130 and a no-puncture zone 135. The guidance mechanism 150 may be utilized to ensure the puncture doesn't occur in the no-puncture zone 135 illustrated in FIGS. 11A-11B. In the illustrated views, the puncture zone 130 may be approximately 1 cm wide. Generally, the imaging device 100 may be positioned during use to ensure that the target location, such as a vessel, is within the no-puncture zone 135 such that the intervention device 100 may be visible both during delivery to the target location and upon arrival at the target location.

However, it should be appreciated that the zones 130, 135 illustrated in FIGS. 11A and 11B are merely for exemplary purposes, and thus should not be construed as limiting in scope. For example, there may be situations in which a physician may desire or need to puncture a vessel with the needle in the no-puncture zone 135. As a further example, the sizes of the respective zones 130, 135, as well as the ratio between their respective sizes, may vary in different embodiments and should not be construed as limited by the example embodiment illustrated in FIGS. 11A and 11B.

The manner by which the guidance mechanism 120, 150 is secured to the imaging device 100 may vary in different embodiments, and thus should not be construed as limited by the example embodiments shown in the figures. In the embodiments shown in FIGS. 4, 10, and 16, it can be seen that the guidance mechanism 120, 150 may be removably attached to the imaging device 100 by the attachment mechanism 110. However, as previously mentioned, the guidance mechanism 120, 150 may in other embodiments be fixedly attached to the imaging device 100 or integral therewith. In embodiments in which the guidance mechanism 150 is integrally formed with the imaging device 100, the guidance mechanism 120, 150 may extend outwardly from a distal portion of the imaging device 100.

FIGS. 6A-7B, 12A-15, 18A-18B, and 20A-21 illustrate example embodiments of an attachment mechanism 110 and guidance mechanism 120, 150. As shown, the attachment mechanism 110 may include an opening 110C into which the imaging device 100 may be removably inserted for use. The shape of the opening 110C may vary in different embodiments, and thus should not be construed as limited by the example embodiments shown in the figures. Generally, the opening 110C may be substantially rectangular, though other shapes may be utilized to suit different types of imaging devices 100.

The size of the opening 110C may also vary in different embodiments, and similarly should not be construed as limited by the example embodiments shown in the figures. Generally, the opening 110C should be sized such that the imaging device 100 may be snugly fit therein. In some embodiments, the imaging device 100 may frictionally engage within the opening 110C such that no tabs 110A, 110B are necessary. In such embodiments, the size of the opening 110C will be slightly smaller than the outer circumference or width of the imaging device 100 to allow for a frictional engagement to maintain the attachment mechanism 110 on the imaging device 100 during use.

The attachment mechanism 110 may include one or more tabs 110A, 110B for aiding in removably attaching the attachment mechanism 110 to the imaging device 100. In the illustrated example embodiments, it can be seen that a first tab 110A may extend upwardly from a first side of the attachment mechanism 110 and a second tab 110B may extend upwardly from a second side of the attachment mechanism 110. However, it should be appreciated that the number of tabs 110A, 110B may vary in different embodiments (e.g., there may be more or less than two tabs 110A, 110B). It should also be appreciated that the positioning of the tabs 110A, 110B on the attachment mechanism 110 may also vary in different embodiments.

As best shown in FIGS. 6A-7B, each tab 110A, 110B may include a curved inner surface which may engage with a curved outer surface of the imaging device 100 as shown in FIG. 4. A projection, such as a handle, may extend angularly from the curved surface such that the projection may be pressed outwardly to disengage the tab 110A, 110B from the imaging device 100 and thus allow the attachment mechanism 110 to be slid off or otherwise removed from the imaging device 100 after use.

Figure 6A:
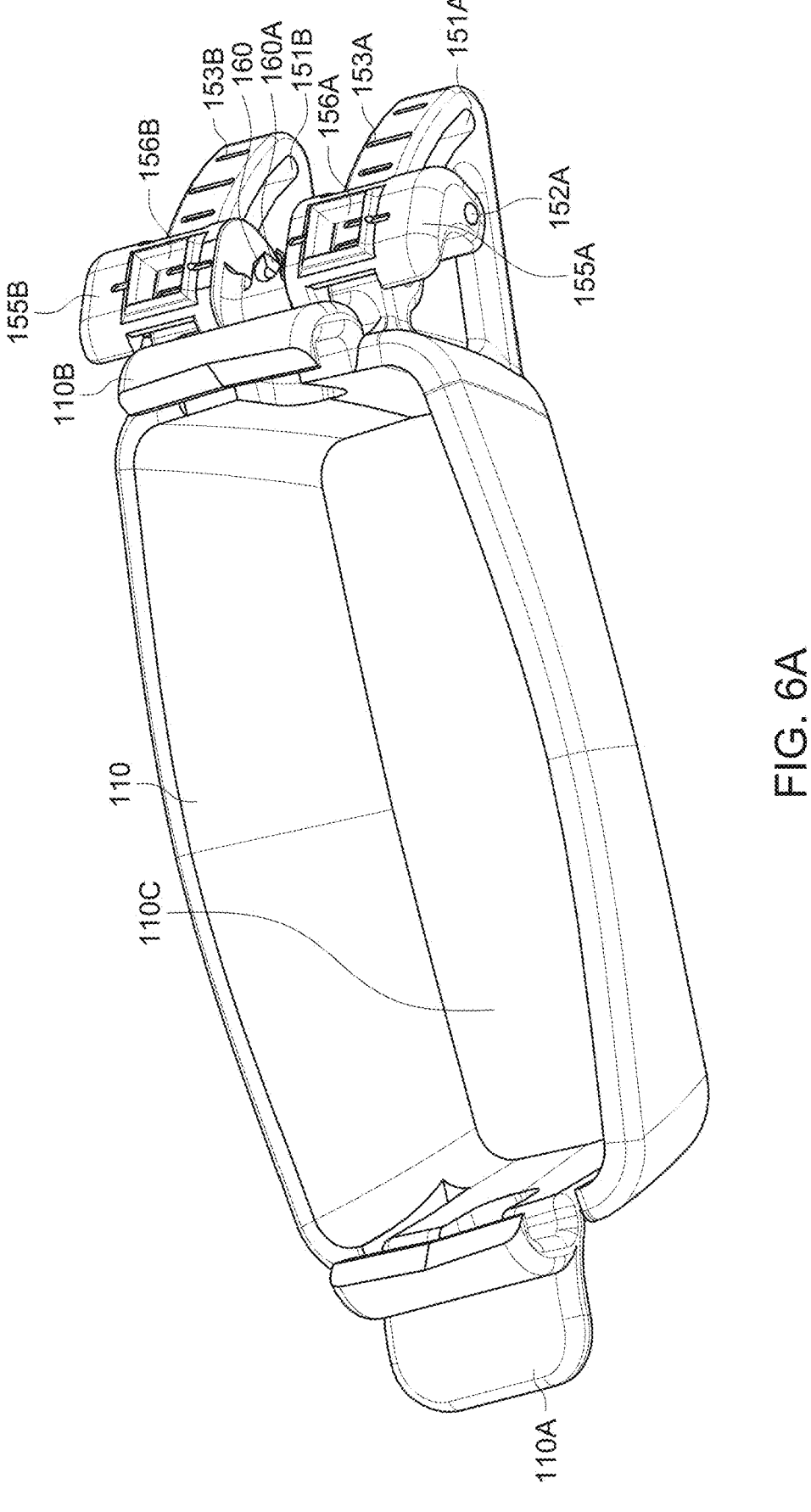
FIG. 6A is a first perspective view of a needle guidance system according to an example embodiment.
Figure 9:
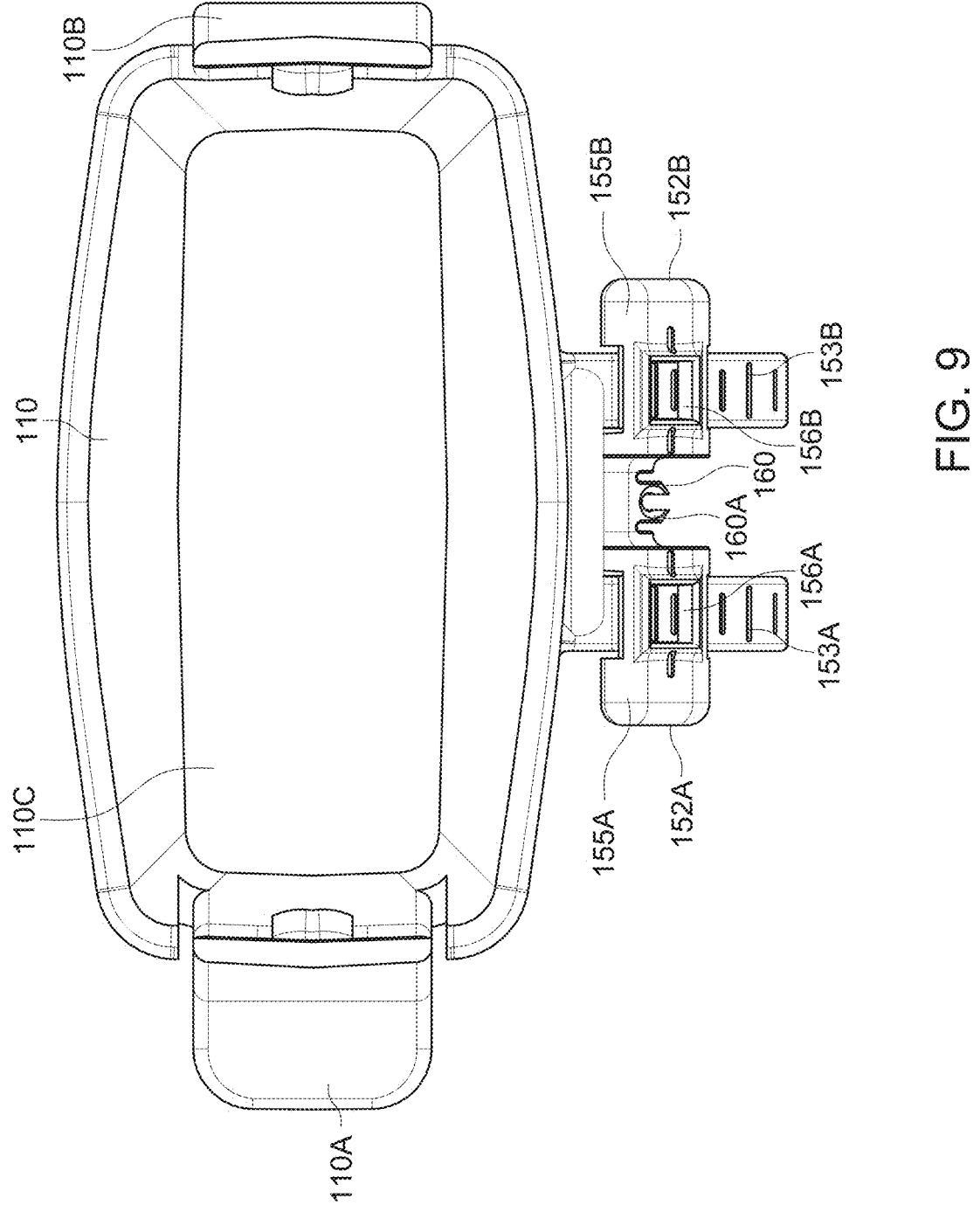
FIG. 9 is a top view of a needle guidance system according to an example embodiment.
Figure 22:
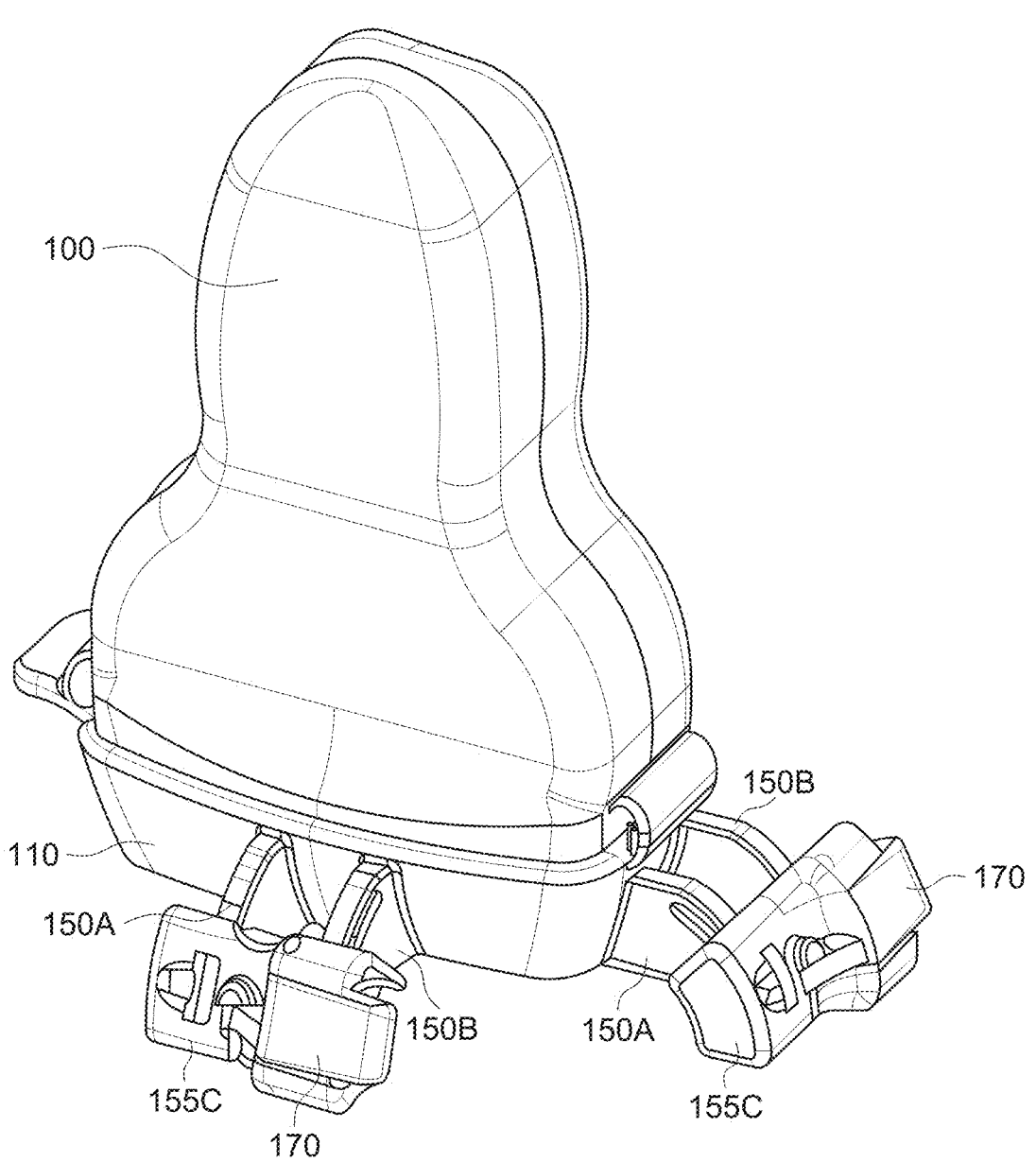
FIG. 22 is a perspective view of a needle guidance system according to an example embodiment.

As shown throughout the figures, at least one guidance mechanism 120 may extend outwardly from the attachment mechanism 110. The positioning and orientation of the guidance mechanism(s) 120 in relation to the body of the attachment mechanism 110 may vary in different embodiments. For example, the example embodiment shown in FIG. 6A illustrates a single guidance mechanism 120 on a side of an attachment mechanism 110. FIG. 9 illustrates a single guidance mechanism 120 instead positioned on an end of an attachment mechanism 110, at a ninety degree angle with respect to the embodiment shown in FIG. 6A. FIGS. 22-23C illustrate example embodiments having a pair of guidance mechanisms 120—one on a side and another on an end. Although not shown, it should be appreciated that, in some embodiments, even more guidance mechanisms 120 may extend from the attachment mechanism 110. For example, three or more guidance mechanisms 120 may instead be utilized to provide additional versatility to be used with a wide range of imaging devices 100 and applications.

Although discussed separately, it should be appreciated that the attachment mechanism 110 and the guidance mechanism 120 may be integrally formed from a unitary structure. However, in other embodiments, the guidance mechanism 120 may instead be fixedly or removably attached to the attachment mechanism 110.

Generally, the guidance mechanism 120 may extend outwardly from a side or an end of the attachment mechanism 110, though other mounting locations may be utilized than are shown in the example embodiments of the figures. The guidance mechanism 120 may generally include one or more openings 120A, 120B, 120C, 120D for guiding an intervention device 200 such as a needle at an optimal angle so as to maintain the intervention device 200 within a field of view of the imaging device 100 during delivery to and arrival at a target location, such as a vessel.

FIGS. 4-9 illustrate an example embodiment of a needle guidance system for guiding an intervention device 200 to a target location while remaining within the field of view of an imaging device 100. In the illustrated example embodiment, it can be seen that a guidance mechanism 150 may comprise a pair of parallel adjustment members 155A, 155B which each extend outwardly from a side of an attachment mechanism 110. Thus, a first arm 150A may extend from a side of the attachment mechanism 110 near its front end and a second arm 150B may extend from the same side of the attachment mechanism 110 near its rear end, parallel to the first arm 150A. The arm 150A, 150B may be parallel and spaced apart so as to define a space between them such as shown in FIG. 11A.

As best shown in FIGS. 6A-7B, each of the arms 150A, 150B may include a track 151A, 151B, with the first arm 150A having a first track 151A and the second arm 150B having a second track 151B. The tracks 151A, 151B may each comprise arcuately oriented slots which function as a guide and track for a pair of adjustment members 155A, 155B as discussed in more detail below.

Continuing to reference FIGS. 6A-7B, it can be seen that the pair of adjustment members 155A, 155B may be movably connected to the arms 150A, 150B, with a first adjustment member 155A being movably connected to the first arm 150A and a second adjustment member 155B being movably connected to the second arm 150B. The adjustment members 155A, 155B may be linked together so that they move together in tandem, such as by a receiver 160 as discussed herein.

Figure 5:
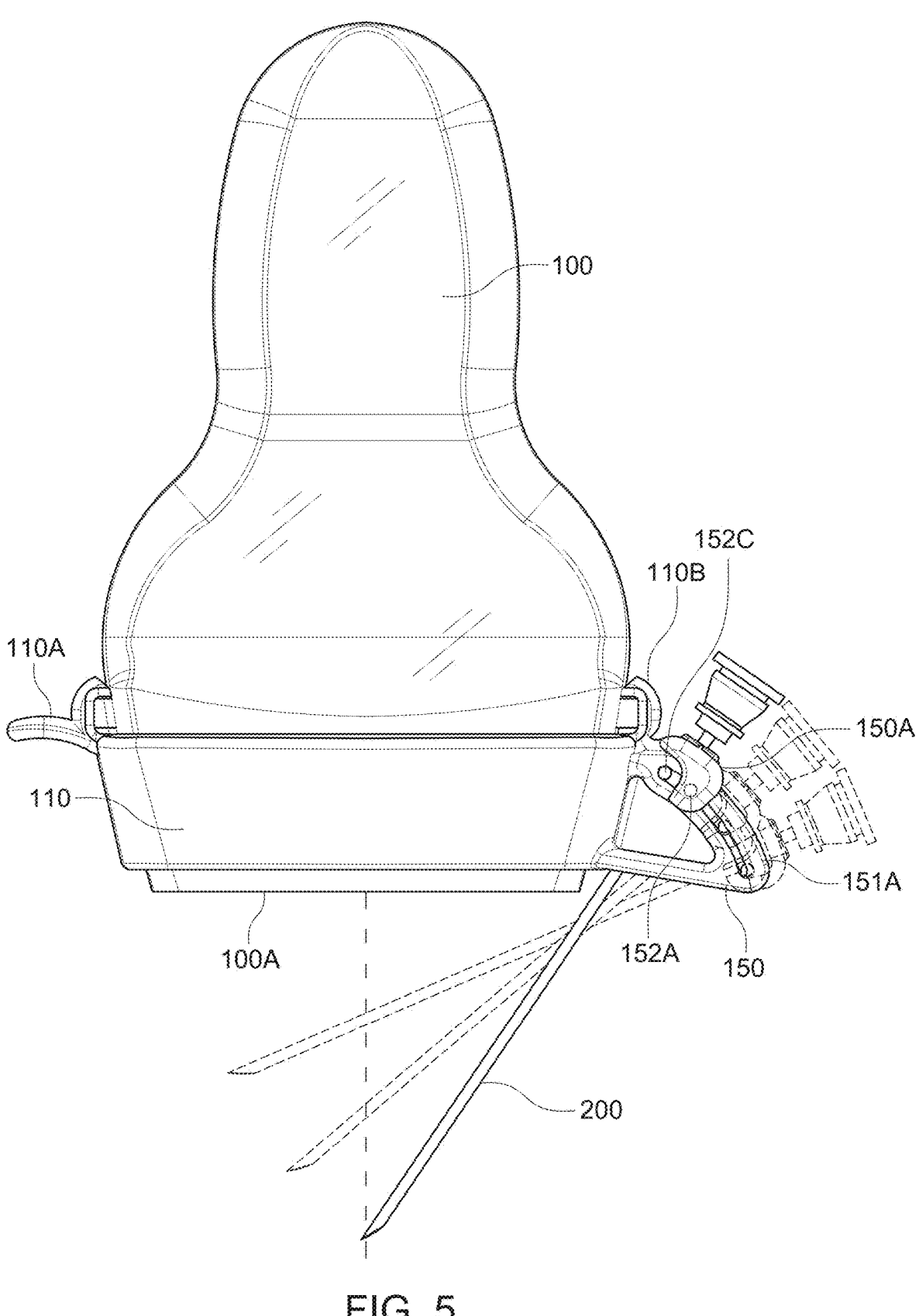
FIG. 5 is a front view of a needle guidance system illustrating multiple needle positions according to an example embodiment.
Figure 6B:
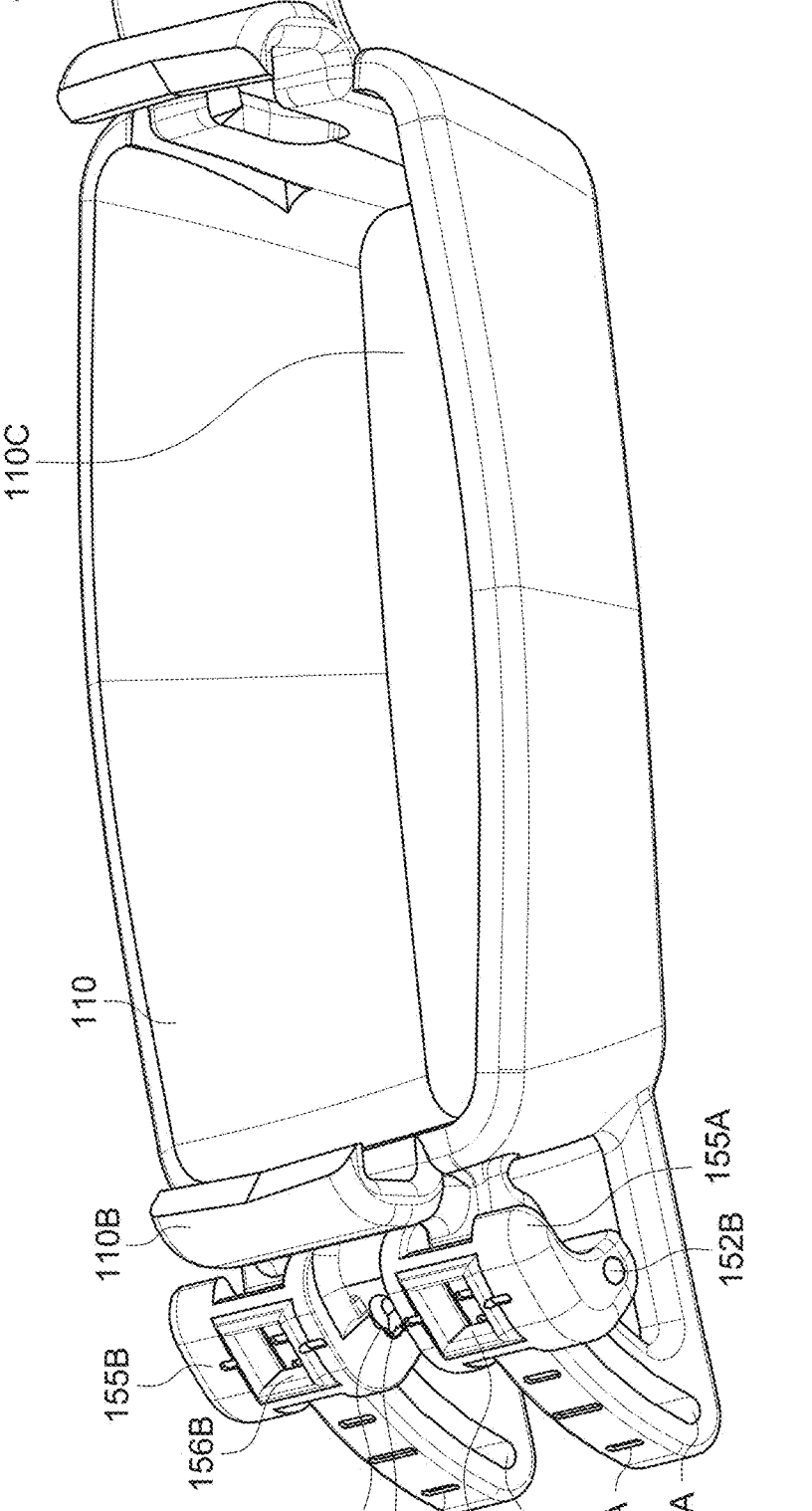
FIG. 6B is a second perspective view of a needle guidance system according to an example embodiment.

As best shown in FIGS. 6A and 6B, the first adjustment member 155A may include a first pin 152A which extends through the first track 151A and the second adjustment member 155B may include a second pin 152B which extends through the second track 151B. As best shown in FIG. 5, a third pin 152C may also pass through both tracks 151A, 151B, but not extend past the outer edge of the tracks 151A, 151B. The pins 152A, 152B, 152C function to movably connect the adjustment members 155A, 155B to the arms 150A, 150B such that the adjustment members 155A, 155B may traverse along an arcuate path defined by the tracks 151A, 151B.

Figure 7A:
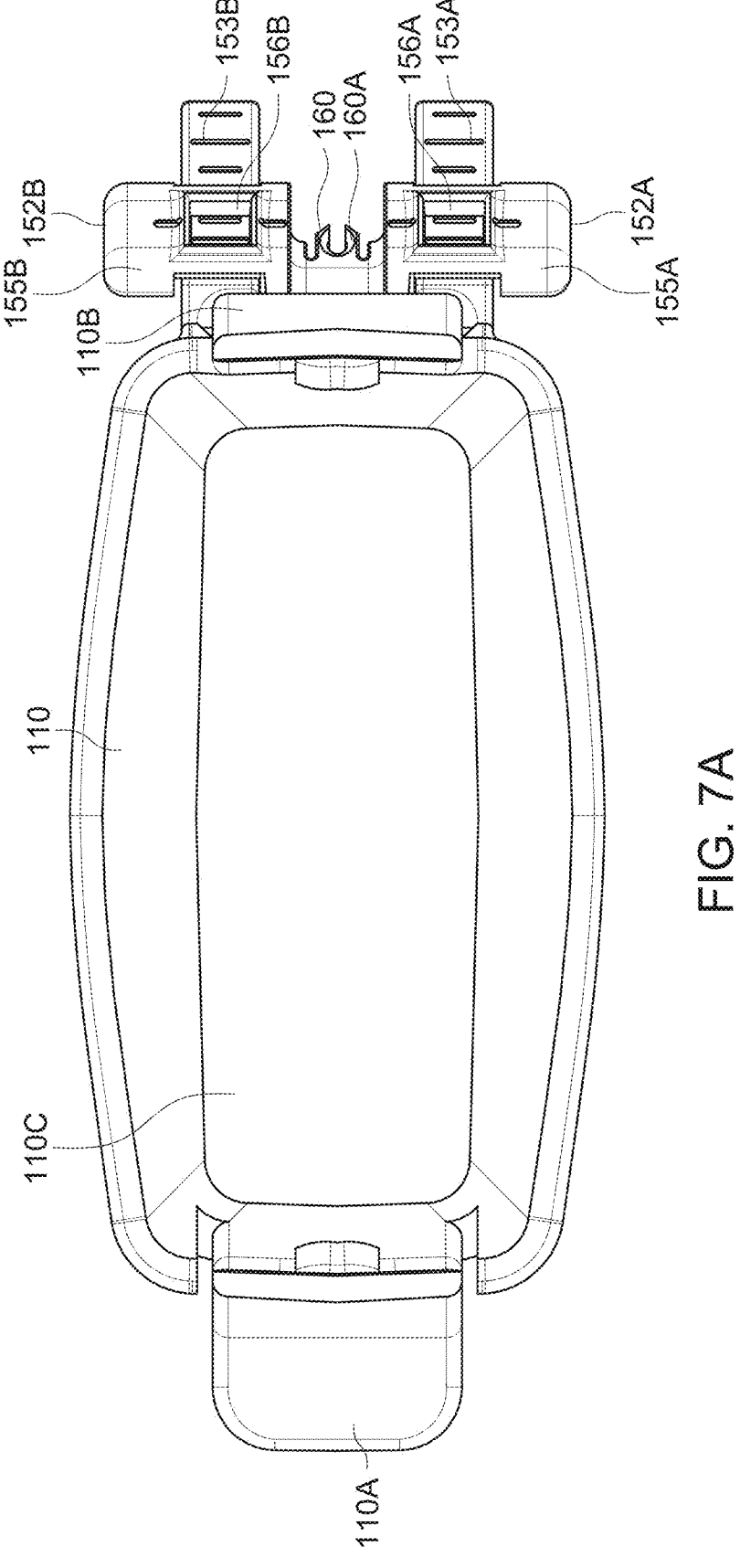
FIG. 7A is a top view of a needle guidance system according to an example embodiment.
Figure 7B:
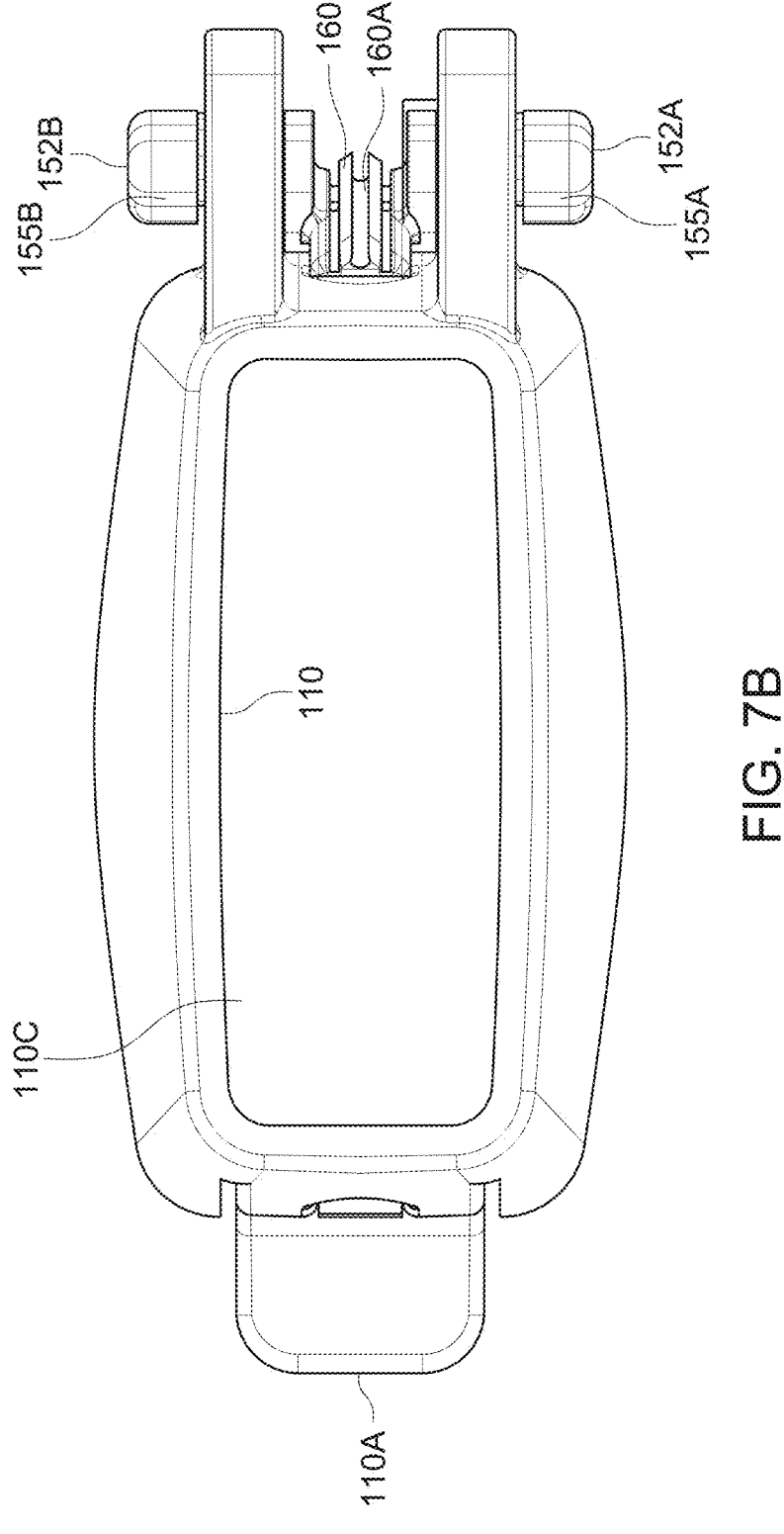
FIG. 7B is a bottom view of a needle guidance system according to an example embodiment.

As best shown in FIG. 7A, each of the arms 150A, 150B may include indicia 153A, 153B to identify different points along the arcuate path along which the arms 150A, 150B traverse during adjustment, with the first arm 150A having a first plurality of indicia 153A and the second arm 150B having a second plurality of indicia 153B. Each indicia 153A, 153B may identify the depth at which the intervention device 200 will cross the centerline of the imaging device 100, measured from the bottom face of the probe 100A.

Each of the adjustment members 155A, 155B may include a window 156A, 156B so that the indicia 153A, 153B can viewed and identified, with the first adjustment member 155A having a first window 156A and the second adjustment member 155B having a second window 156B. While the windows 156A, 156B are illustrated as being rectangular, it should be appreciated that other shapes may be utilized.

As best shown in FIGS. 7A-9, a receiver 160 may be connected between the adjustment members 155A, 155B in the gap or space between the arms 150A, 150B. The receiver 160 may comprise a receiver opening 160A for receiving the intervention device 200, such as a needle or the like. The receiver opening 160A may comprise an elongated opening such as a slot through which the intervention device 200 may be inserted and removed from the receiver opening 160A.

Figure 8:
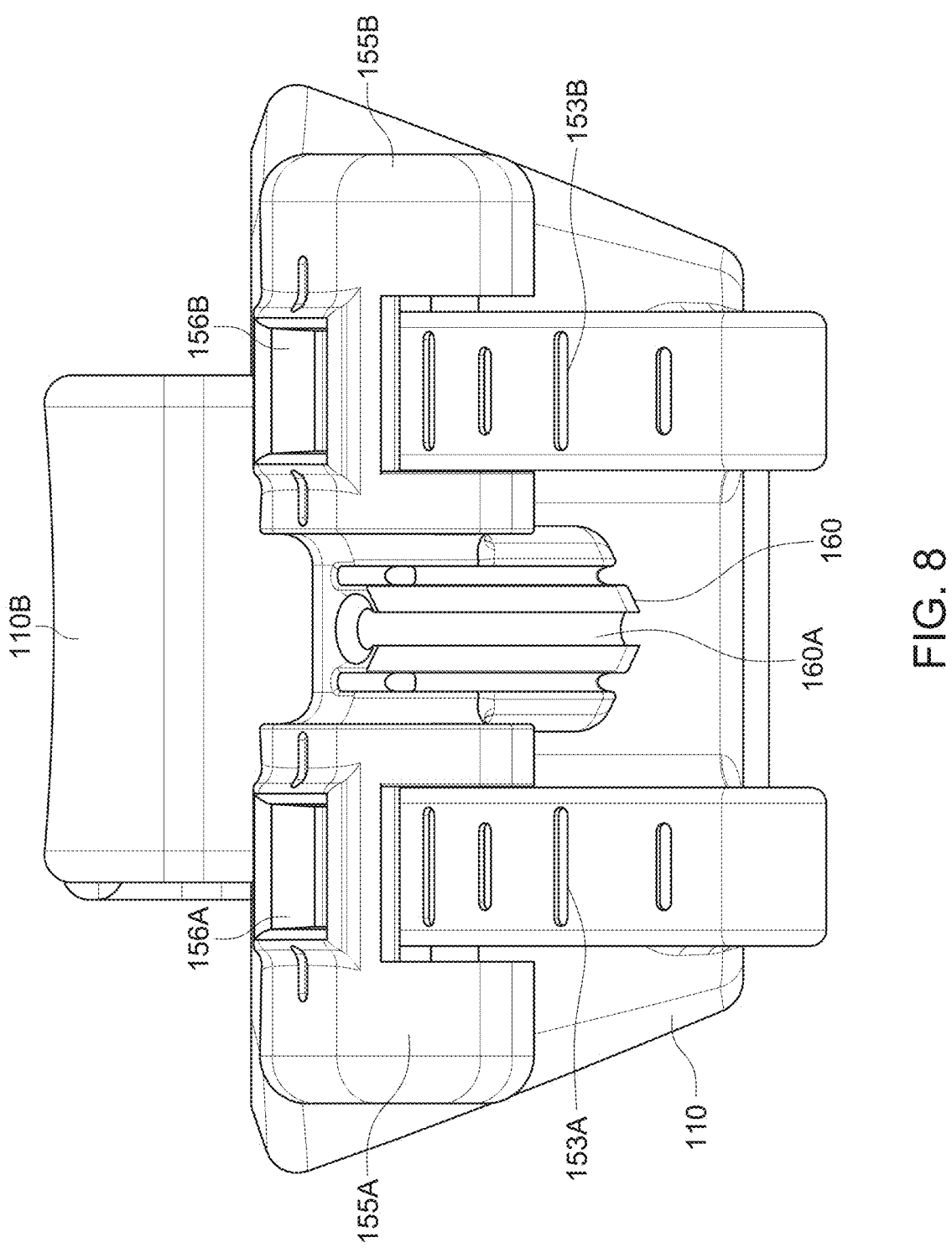
FIG. 8 is a front view of an adjustment mechanism of a needle guidance system according to an example embodiment.

As shown in FIGS. 8-9, the receiver opening 160A may include flaps which define the elongated opening through which the intervention device 200 may be inserted or removed. The flaps may comprise a flexible or semi-flexible, resilient material such that the flaps adjust outwardly to allow the intervention device 200 to be removed from the receiver opening 160A.

In use, the imaging device 100 may be positioned over the target location on the skin of the patient, with the target location being within the field of view of the imaging device 100. The adjustment members 155A, 155B may be adjusted along the arcuate path of the tracks 151A, 151B until a desired depth is reached, with the depth being represented by the indicia 153A, 153B visible through the windows 156A, 156B. Before or after adjusting the adjustment members 155A, 155B, the intervention device 200 may be inserted into the receiver 160 through the receiver opening 160A.

The intervention device 200 may then be advanced to the target location, with the intervention device remaining within the field of view of the imaging device both during delivery and upon reaching the target location. After the intervention device 200 has reached its target location, such as upon puncturing a vessel, the intervention device 200 may be removed from the guidance mechanism 150 without movement of the intervention device 200. The guidance mechanism 150 may be moved away, with the flaps of the receiver opening 160A adjusting outwardly to allow the intervention device 200 to be removed from the receiver 160 and then resiliently returning to their original position.

FIGS. 10-12B illustrate an example embodiment of a needle guidance system for guiding an intervention device 200 to a target location while remaining within the field of view of an imaging device 100. As best shown in FIGS. 10-11B, a plurality of openings 120A, 120B, 120C, 120D may extend through the guidance mechanism 120 at different angles. However, only a single opening 120A, 120B, 120C, 120D may be utilized in some embodiments. While the figures illustrate four such openings 120A, 120B, 120C, 120D, comprised of a first opening 120A, a second opening 120B, a third opening 120C, and a fourth opening 120D, it should be appreciated that more (e.g., five or more) or less (e.g., three or less) openings 120A, 120B, 120C, 120D may be utilized in different embodiments.

The angles of each of the openings 120A, 120B, 120C, 120D may vary in different embodiments and should not be construed as limited by the figures. As best shown in FIGS. 11A and 11B, each opening 120A, 120B, 120C, 120D may correspond with a different depth of the intervention device 200. An appropriate opening 120A, 120B, 120C, 120D may be selected by an operator of the present invention depending upon the position (e.g., depth and angle) of the target location with respect to the imaging device 100.

Generally, each of the openings 120A, 120B, 120C, 120D may be sized to receive an intervention device 200 such as a needle as shown in FIGS. 11A and 11B. The size of the openings 120A, 120B, 120C, 120D may vary in different embodiments to suit different gauges of different intervention devices 200. For example, for an 18-gauge needle having an approximate diameter of 1.3 mm, the openings 120A, 120B, 120C, 120D may each have a diameter of between 1.3 mm-1.4 mm to ensure that the needle does not jostle within the opening 120A, 120B, 120C, 120D.

Figure 13:
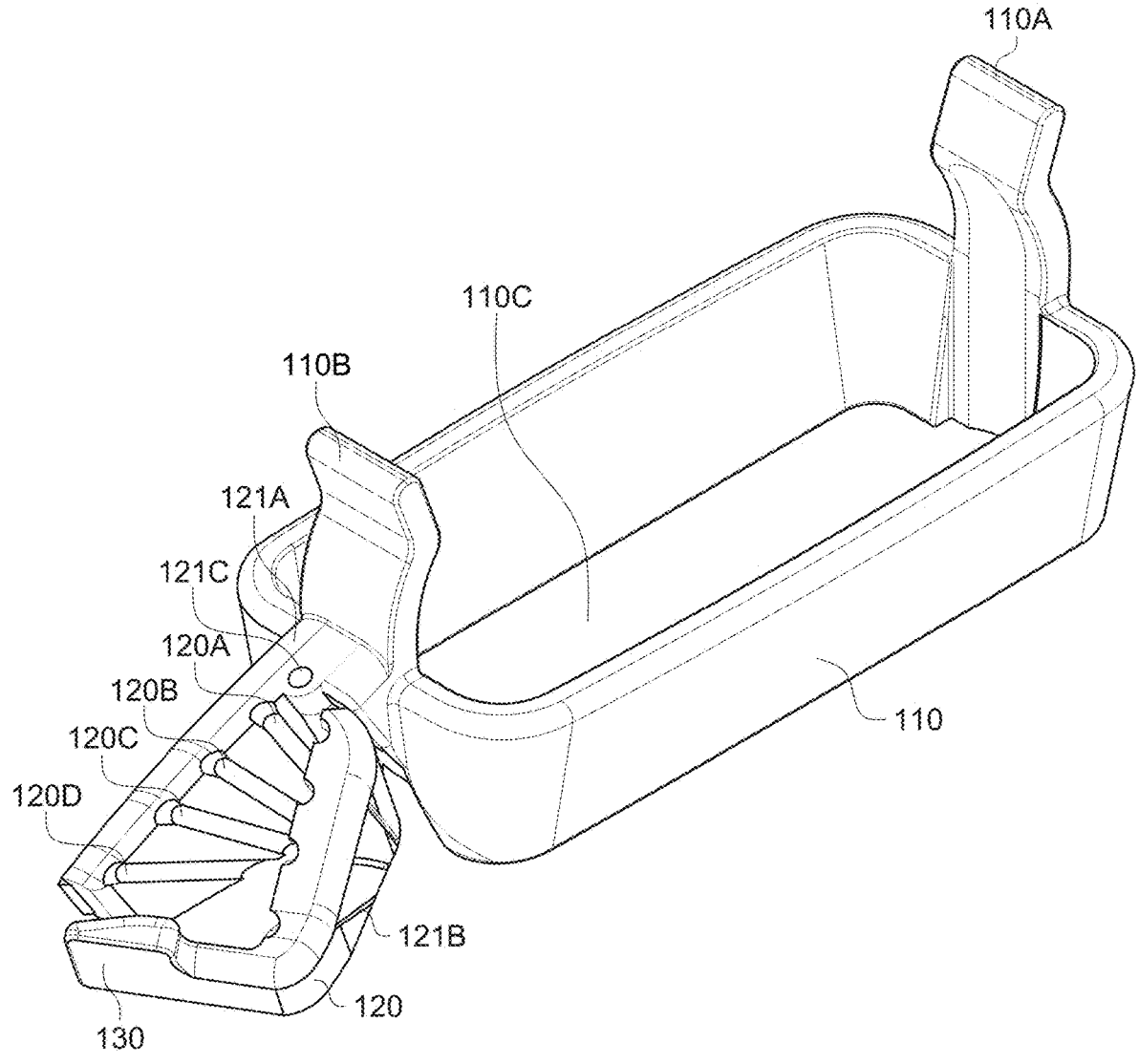
FIG. 13 is a perspective view of a needle guidance system illustrating a needle release mechanism according to an example embodiment.
Figure 14A:
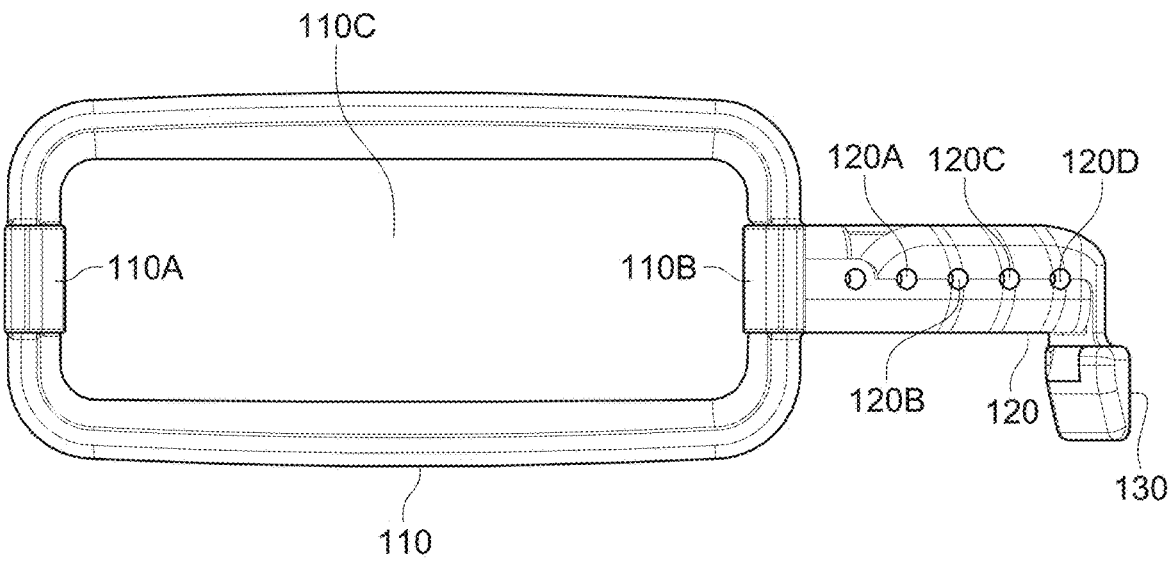
FIG. 14A is a top view of a needle guidance system according to an example embodiment.
Figure 14B:
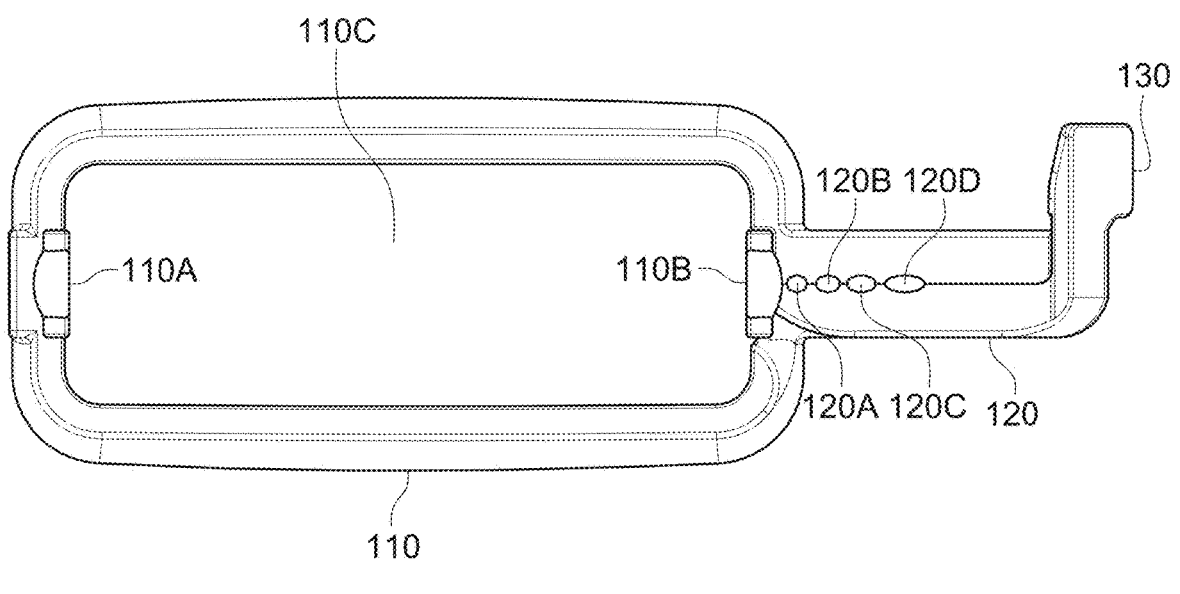
FIG. 14B is a bottom view of a needle guidance system according to an example embodiment.

As best shown in FIG. 13, the guidance mechanism 120 may include a release mechanism such that the intervention device 200 may be easily removed from the guidance mechanism 120 without moving the intervention device 200 after it has reached its target location. In an example embodiment, the guidance mechanism 120 may comprise a first, fixed portion 121A and a second, adjustable portion 121B. The second portion 121B may be adjustable towards or away from the first portion 121A such that the guidance mechanism 120 may be opened to release the intervention device 200.

Continuing to reference FIG. 13, the first and second portions 121A, 121B of the guidance mechanism 120 may be hingedly connected by a pivot pin 121C or the like. In the illustrated embodiment, the second portion 121B is hingedly or pivotably attached to the first portion 121A by the pivot pin 121C such that the second portion 121B may be pivoted towards or away from the first portion 121A. However, it should be appreciated that, in some embodiments, various other methods of adjustment may be utilized other than pivoting.

Figure 12A:
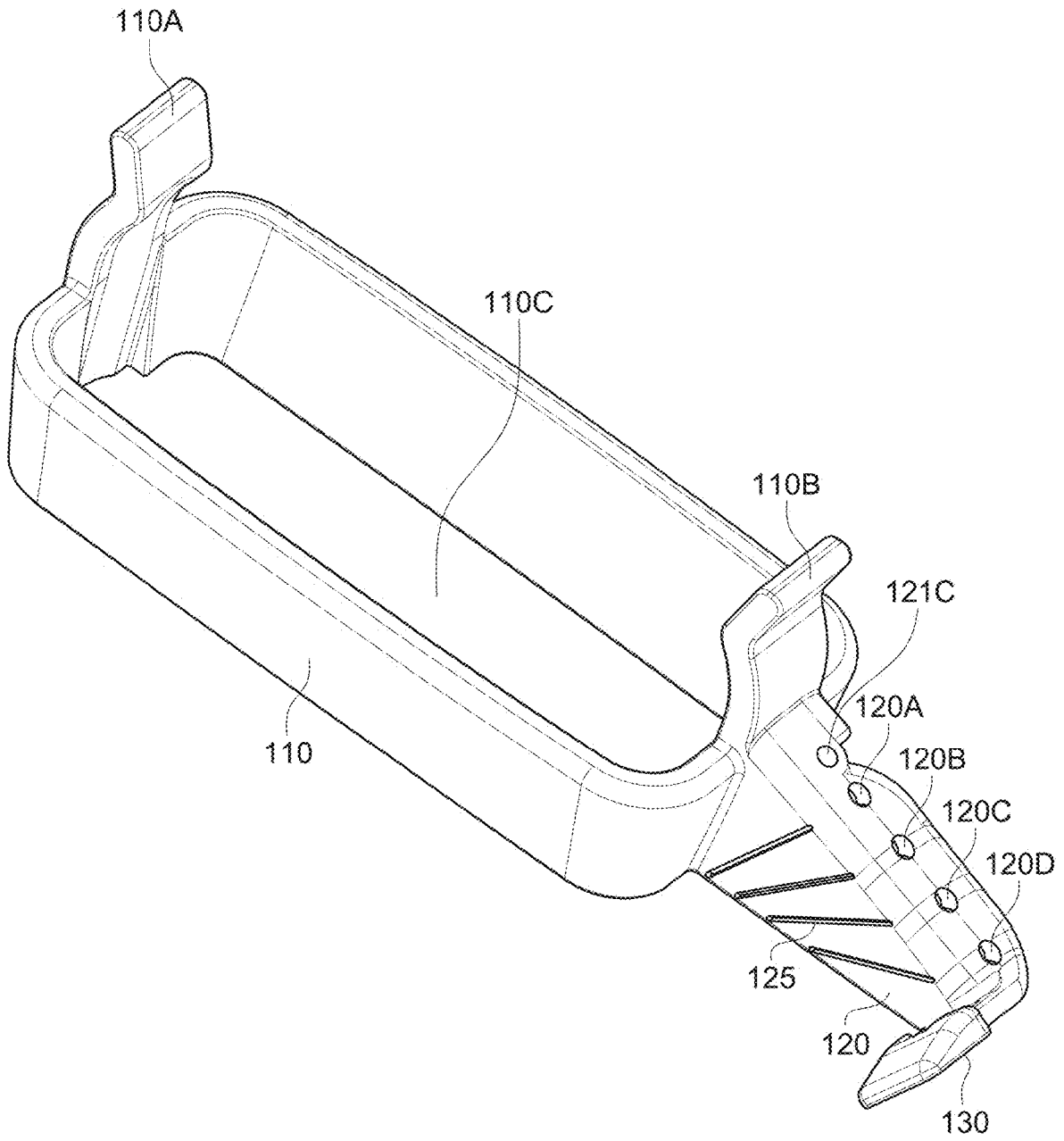
FIG. 12A is a first perspective view of a needle guidance system according to an example embodiment.
Figure 12B:
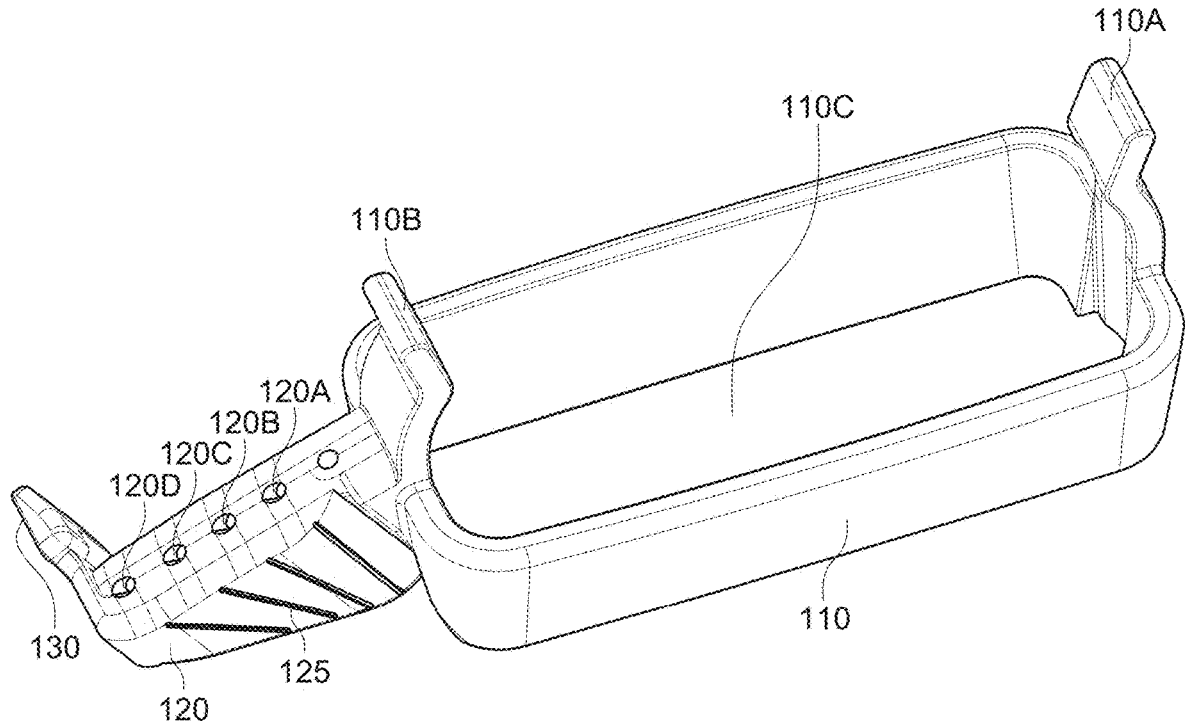
FIG. 12B is a second perspective view of a needle guidance system according to an example embodiment.

As best shown in FIGS. 12A and 12B, the guidance mechanism 120 may include indicia 125 to indicate the different angles of each opening 120A, 120B, 120C, 120D. The indicia 125 may comprise markings, grooves, or the like which provide a visual indication of the relevant angle of each 120A, 120B, 120C, 120D. The indicia 125 may be located on an outer surface of the guidance mechanism 120 so as to be easily visible during use.

Each of the first and second portions 121A, 121B may include a semi-circular opening which, when brought together, form the openings 120A, 120B, 120C, 120D for guiding the intervention device 200. A locking member such as a clasp or the like may removably secure the two portions 121A, 121B together such that grasping the locking member 121D releases the portions 121A, 121B from each other to allow the intervention device 200 to be removed. Releasing the locking member allows the second portion 121B to pivotably swing away from the first portion 121A to release the intervention device 200.

In use, the attachment mechanism 110 may first be attached to the imaging device 100. For example, the probe 100A of the imaging device 100 may be inserted within the opening 110C of the attachment mechanism 110 to the point where the tabs 110A, 110B of the attachment mechanism 110 engage with the outer edges of the imaging device 100. The imaging device 100 may then be positioned over the skin of a patient such that the target location, such as a vessel, is within its field of view.

The operator may then select one of the openings 120A, 120B, 120C, 120D of the guidance mechanism 120 based on the depth of the target location, with the optimal opening 120A, 120B, 120C, 120D ensuring that the intervention device 200 remains within the puncture zone shown in FIGS. 2A and 2B during both delivery to and arrival at the target location. Once an opening 120A, 120B, 120C, 120D is selected, the intervention device 200 may be inserted therethrough and delivered to the target location with guidance provided by an image produced by the imaging device 100.

Upon arrival of the intervention device 200 at the target location, such as upon puncturing a vessel, the operator may disengage the locking member 121D and move the second portion 121B of the guidance mechanism 120 away from the first portion 121A of the guidance mechanism 120. With the release engaged in such a manner, the guidance mechanism 120 may be removed from around the intervention device 200 without moving the intervention device 200.

FIGS. 16-18B illustrate another example embodiment of a needle guidance system. The example embodiment shown in FIGS. 16-18B may utilize a single opening 140A rather than a plurality of openings, with the angular position of the single opening 140A being adjustable through use of an adjustment mechanism 140 that is movably connected to the guidance mechanism 120.

Figure 18A:
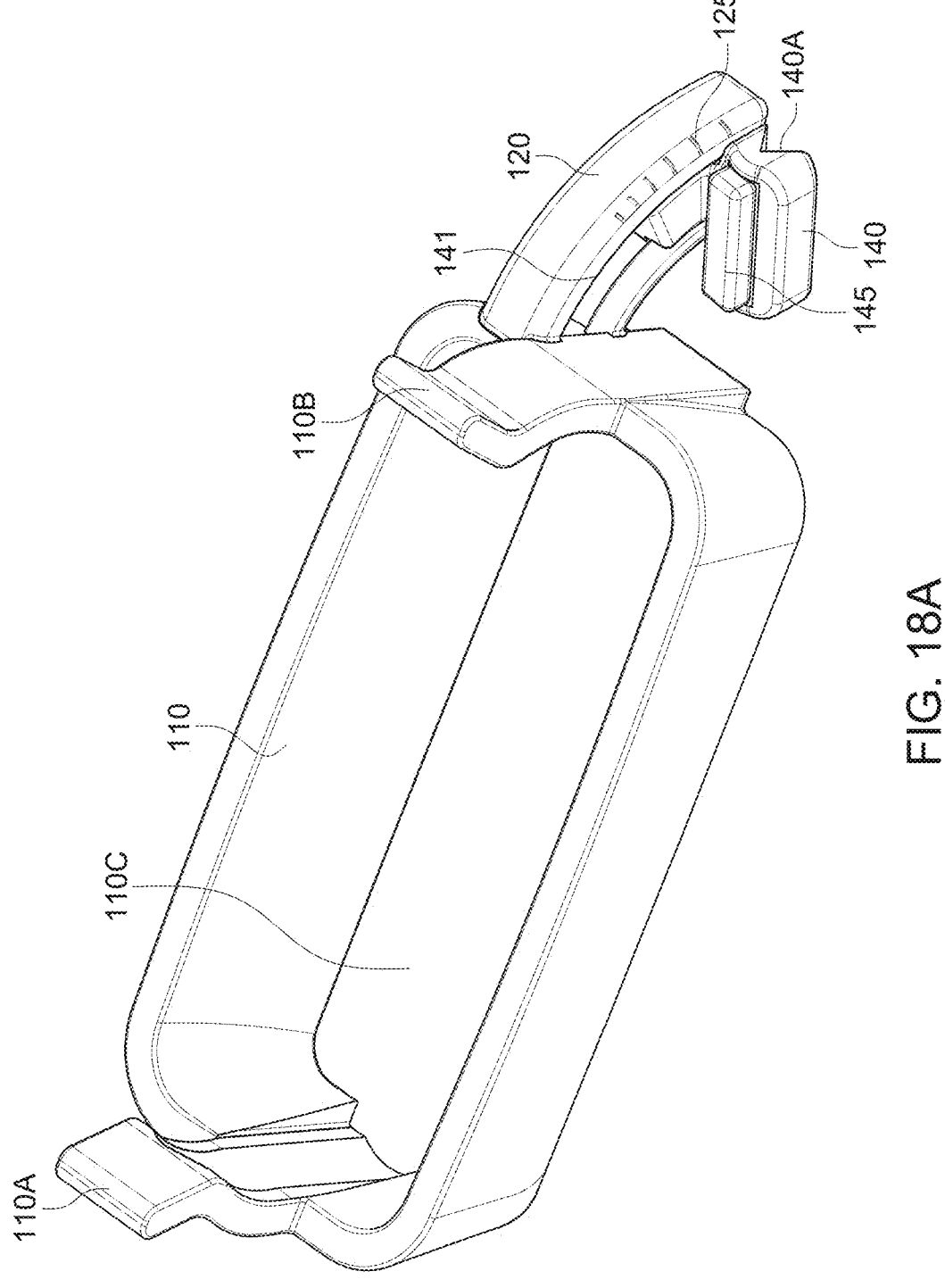
FIG. 18A is a first perspective view of a needle guidance system according to an example embodiment.
Figure 18B:
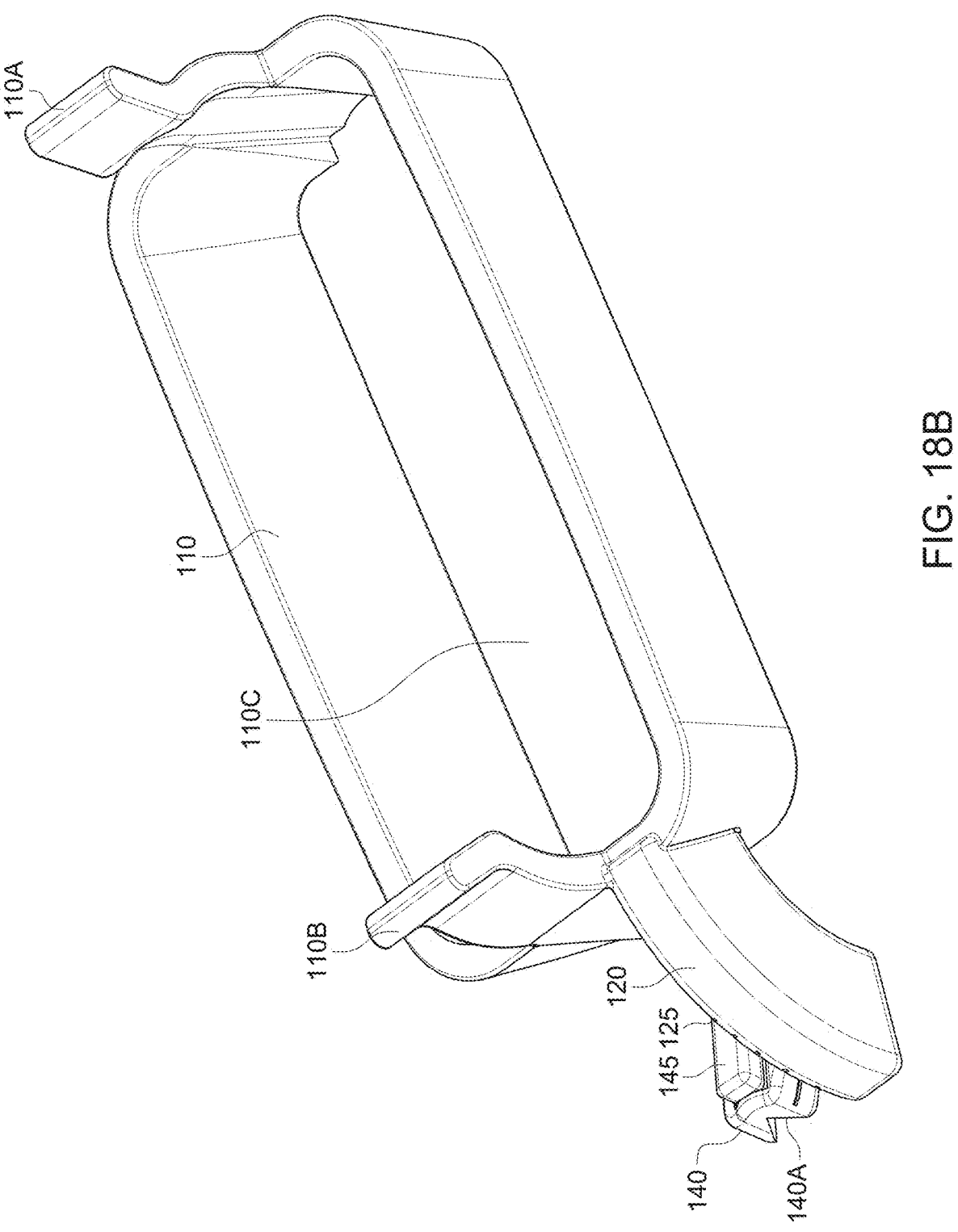
FIG. 18B is a second perspective view of a needle guidance system according to an example embodiment.

As best shown in FIG. 18A, the guidance mechanism 120 may include a track 141 along which an adjustment mechanism 140 may move between different arcuate positions and angular orientations. The track 141 may comprise a slot formed within the guidance mechanism 120. In the illustrated embodiment, it can be seen that the slot may follow an arcuate path. The adjustment mechanism 140 may be slidably positioned within the track 141 such that the adjustment mechanism 140 may be adjusted with respect to the guidance mechanism 120 along the arcuate path.

Continuing to reference FIG. 18A, it can be seen that the adjustment mechanism 140 may include an opening 140A for receiving the intervention device 200, with the positioning and orientation of the opening 140A being adjustable by moving the adjustment mechanism 140 along the track 141. The opening 140A may comprise a slot as shown in the figures, or an enclosed aperture. In the example embodiment shown in FIG. 7A, the opening 140A is illustrated as comprising a V-shaped slot in which the intervention device 200 may be frictionally secured.

The guidance mechanism 120 may include indicia 125 at various intervals to represent different depths and angles for the intervention device 200. Thus, the indicia 125 may indicate the depth at which the intervention device 200 will cross the centerline of the imaging device 100, measured from the bottom face of the probe 100A.

While the indicia 125 provides a visual indication of the depths and angles, it should be appreciated that auditory or tactile indications may also be provided. For example, the guidance mechanism 120 may "click" upon passing each preset interval along the arcuate path of the guidance mechanism 120 while traversing the track 141.

In some example embodiments, the adjustment mechanism 140 may be locked into different positions along the track 141. Various methods known in the art for temporarily locking the adjustment mechanism 140 in a given arcuate position along the track 141 may be utilized, such as projections, openings, clamps, and the like.

A release such as a button or the like may be utilized to release the adjustment mechanism 140 and allow it to move along the track 141. In some example embodiments, the adjustment mechanism 140 may default into a locked position and only be released for movement along the track 141 when the release is engaged, such as pressing down on a button. In other example embodiments, the adjustment mechanism 140 may default into an unlocked position and only be locked by engaging a locking mechanism, such as pressing down on a button.

FIGS. 19A and 19B illustrate an exemplary method for releasing the intervention device 200 from the adjustment mechanism 140 without excessive movement of the intervention device 200. Due to the shape and configuration of the opening 140A, the intervention device 200 may be simply slid out of the opening 140A or, alternatively, the guidance mechanism 120 may be moved so as to release the intervention device 200 from the adjustment mechanism 140.

In one example embodiment, the opening 140A may have a slot through which the intervention device 200 may pass when the guidance mechanism 150 is moved away from the intervention device 200. In some embodiments, the opening 140A may include a flexible, resilient member which deforms so as to allow the intervention device 200 to pass out of the opening 140A before reverting back to its original shape. For example, a pair of resilient flaps may adjust outwardly to allow the intervention device 200 to pass therethrough before resiliently adjusting inwardly to their original position.

In another example embodiment, the opening 140A may comprise a V-shaped slot such as best shown in FIGS. 18A-21. In such an embodiment, as best shown in FIGS. 18A, 18B and 20A, a magnetic element 145 such as a magnet may be positioned within or near the opening 140A so as to magnetically engage with the intervention device 200 when the intervention device 200 is positioned within the opening 140A.

In the illustrated example embodiment, the magnetic element 145 may be attached to the adjustment mechanism 140 behind the opening 140A. The magnetic element 145 will preferably be of sufficient strength to maintain positioning of the intervention device 200 within the opening 140A during use while still allowing the intervention device 200 to be magnetically disengaged when the guidance mechanism 120 is moved away after delivery of the intervention device 200 to the target location. The magnetic element 145 may also function to aid in keeping the intervention device 200 within the field of view of the imaging device 100.

In use, the imaging device 100 may be positioned over the target location on the skin of the patient, with the target location being within the field of view of the imaging device 100. The adjustment mechanism 140 may be adjusted along the track 141 until reaching a desired position coinciding with an appropriate depth. The intervention device 200 may be inserted into the opening 140A and advanced to the target location. Upon arrival at the target location, the intervention device 200 may be released by moving the guidance mechanism 120 away from the intervention device 200 such that the intervention device 200 is released from the opening 140A.

As previously discussed, the positioning and orientation of the guidance mechanism 120 with respect to the body of the attachment mechanism 110 may vary in different embodiments. Further, the number of guidance mechanisms 120 may also vary. Variations in the positioning, orientation, and number of guidance mechanism(s) 120 may allow for additional versatility with respect to the positioning and orientation of the imaging device 100. For example, certain arrangements may be better suited for short access and other arrangements may be better suited for long access. Some configurations as discussed below may allow for both short and long access to be performed with the same device.

Figure 15:
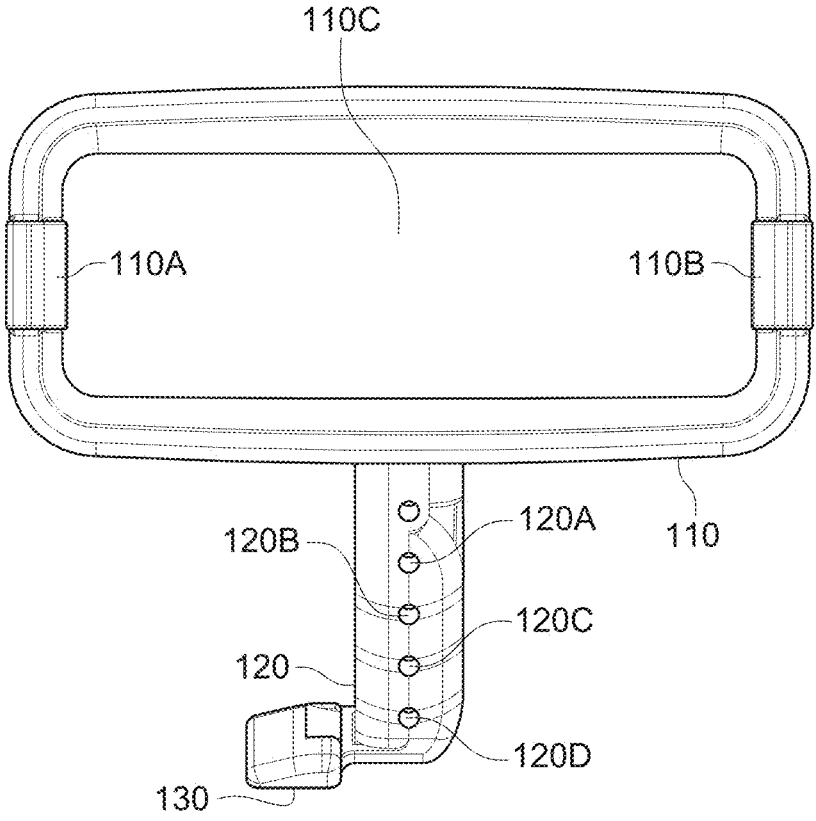
FIG. 15 is a top view of a needle guidance system according to an example embodiment.
Figure 16:
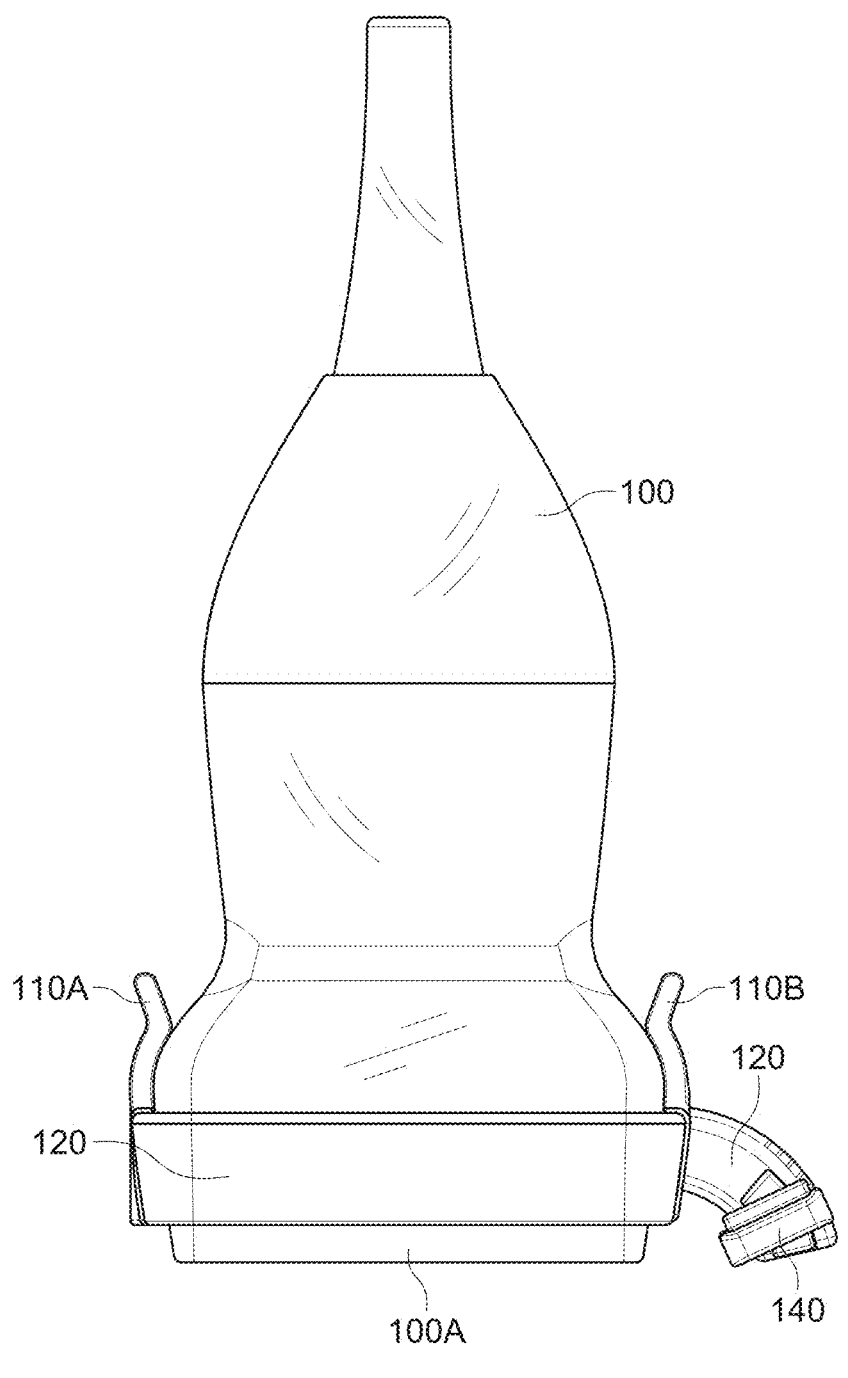
FIG. 16 is a front view of a needle guidance system according to an example embodiment.
Figure 21:
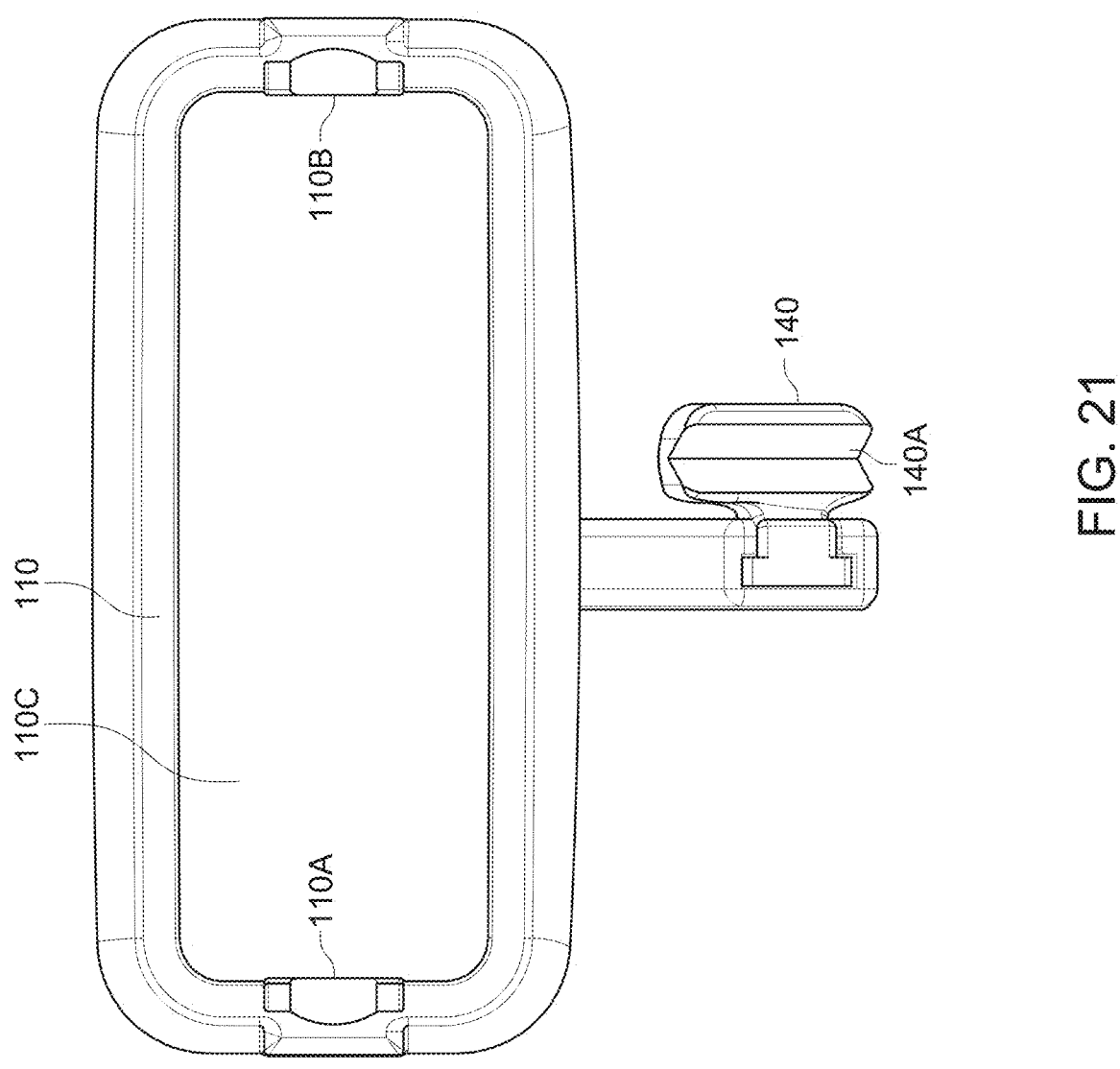
FIG. 21 is a bottom view of a needle guidance system according to an example embodiment.

FIGS. 7A, 7B, 14A, 14B, 20A, and 20B illustrate a single guidance mechanism 120 being attached to or extending from a side of the attachment mechanism 110. FIGS. 9, 15, and 21 illustrate a single guidance mechanism 120 being attached to or extending from an end of the attachment mechanism 110, at a ninety degree angle with respect to one of its sides.

FIGS. 23A-23C and 27A-27B illustrate multiple guidance mechanisms 120 being attached to or extending from the attachment mechanism 110, including a first guidance mechanism 120 on a side of the attachment mechanism 110 and a second guidance mechanism 120 on an end of the attachment mechanism 110 at a ninety degree angle with respect to the first guidance mechanism 120. It should also be appreciated that three or more guidance mechanisms 120 may be utilized in some embodiments to provide for even more versatility.

It should be appreciated that the positioning, orientation, and number of guidance mechanisms 120, 150 may vary for all embodiments shown in the figures or described herein. Thus, for example, the embodiment shown in FIGS. 4-9 may utilize more guidance mechanisms 150 than are shown or may utilize different positioning/orientation of its guidance mechanism 150. Similarly, the embodiment shown in FIGS. 10-15 and the embodiment shown in FIGS. 16-21, may utilize more guidance mechanisms 150 than are shown or may utilize different positioning/orientation of its guidance mechanism 120.

FIGS. 22-23C illustrate an embodiment having multiple guidance mechanisms 150 extending from a single attachment mechanism 110. Such an embodiment may utilize two sets of arms 150A, 150B, with a first set of arms 150A, 150B being perpendicularly oriented with respect to a second set of arms 150A, 150B. Such a configuration may enable transverse access perpendicular to the imaging device's 100 field of view. By utilizing transverse access, shallower depths may be supported, such as between 0.5 cm and 2 cm. However, it should be appreciated that the methods and systems described and/or shown in herein may support depths of less than 0.5 cm or greater than 2 cm.

Instead of the usage of pins 152A, 152B for coupling the guide members 155A, 155B to the arms 150A, 150B, the embodiment shown in FIGS. 22-23C may instead utilize elongated bosses which protrude from a single, unified guide member 155C in the tracks 151A, 151B. Such a configuration may negate the need for a through-hole on the arms 150A, 150B, which increases the strength of the arms 150A, 150B and the guidance mechanism 150 overall. The single, unified guide member 155C may be connected across a pair of arms 150A, 150B as shown in the figures.

Continuing to reference FIGS. 22-23C, it can be seen that such an example embodiment may include a locking mechanism 170 for locking the guide member 155C at various positions along the arms 150A, 150B and a hinged needle release mechanism 180 which enables radial release of the intervention device 200. In some embodiments, locking of the needle release mechanism 180 may also function to lock the locking mechanism 170. In this manner, when an intervention device 200 is locked within the guidance mechanism 150, the guide member 155C will also be locked in place and prevented from moving along the tracks 151A, 151B. Thus, translation of the guidance mechanism 150 relative to the attachment mechanism 110 may be prevented.

Figure 23A:
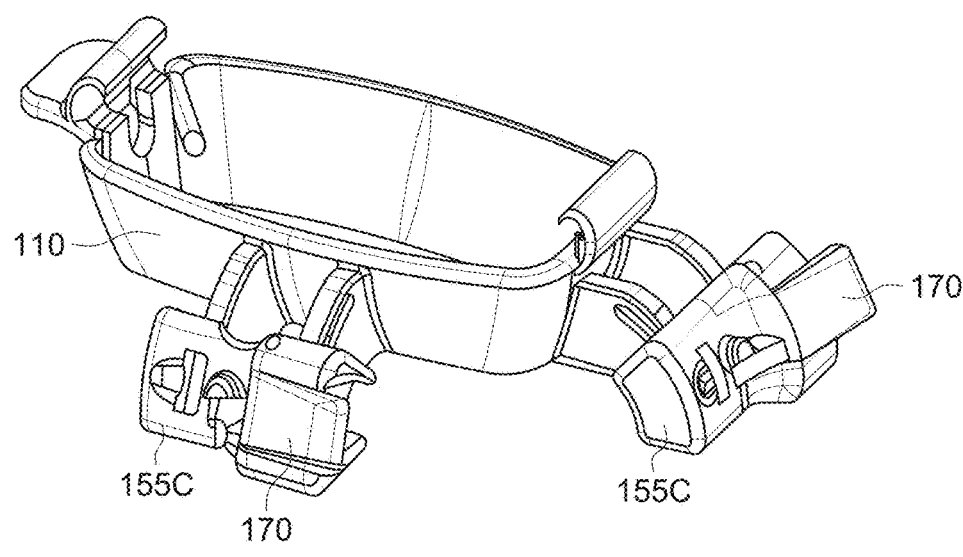
FIG. 23A is a perspective view of a needle guidance system in a first position according to an example embodiment.
Figure 23B:
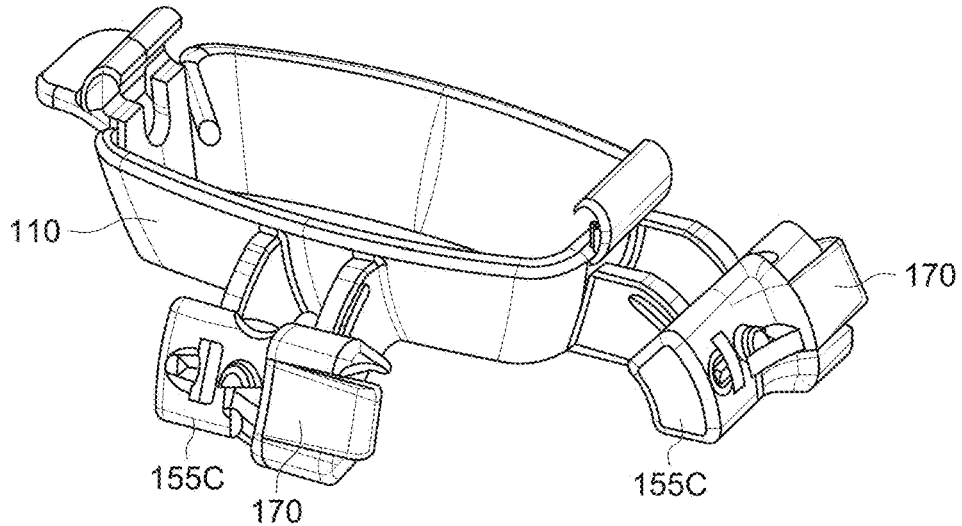
FIG. 23B is a perspective view of a needle guidance system in a second position according to an example embodiment.
Figure 23C:
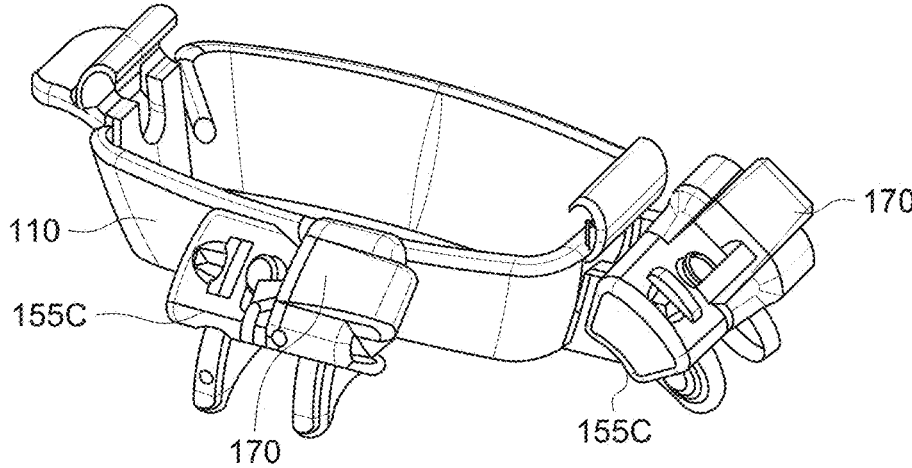
FIG. 23C is a perspective view of a needle guidance system in a third position according to an example embodiment.

FIGS. 23A-23C illustrate different operational states of such an embodiment. FIG. 23A illustrates an unlocked operational state. FIG. 23B illustrates an unlocked state, with both guidance mechanisms 150 being at the shallowest depth setting. FIG. 23 illustrates an unlocked state, with both guidance mechanisms 150 being at the deepest depth setting.

Figure 24A:
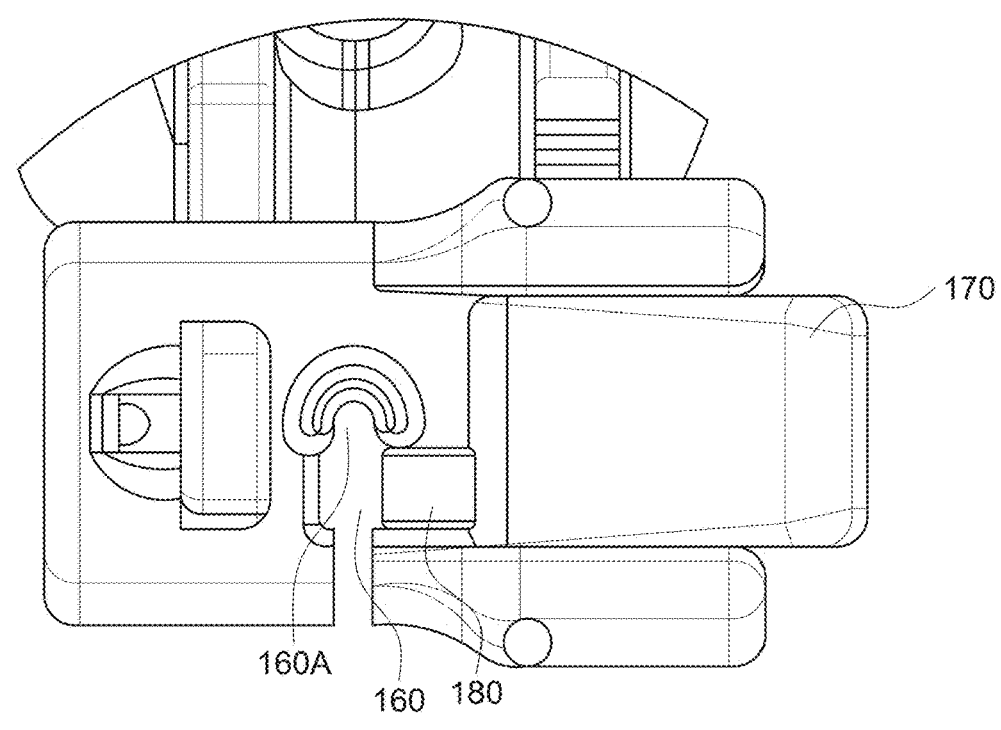
FIG. 24A is a front view of a release mechanism of a needle guidance system in a first position according to an example embodiment.
Figure 24B:
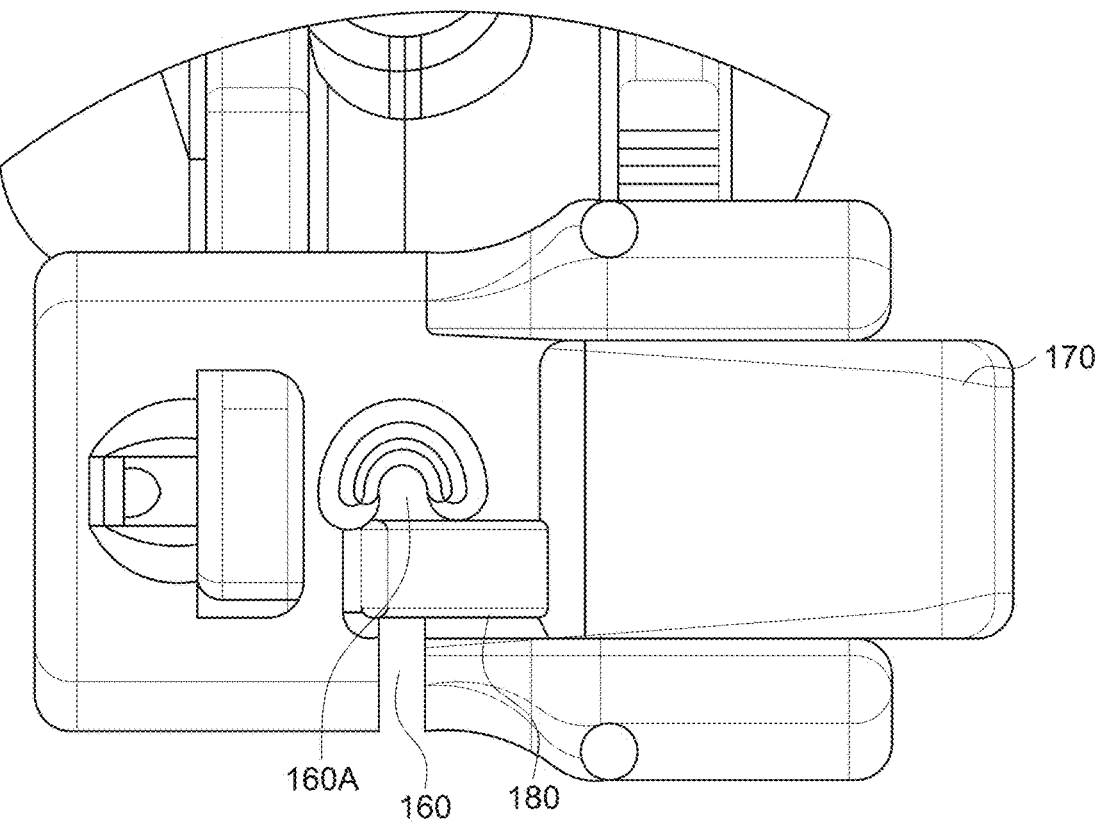
FIG. 24B is a front view of a release mechanism of a needle guidance system in a second position according to an example embodiment.

FIGS. 24A and 24B illustrate a closer view of a single, unified guide member 155C which traverses a pair of arms 150A, 150B at a right angle. As shown, the guide member 155C may include a locking mechanism 170 which may be adjusted, such as linearly, pivotally, or otherwise, between an opened state and a closed, locked state. Attached to the locking mechanism 170 is a release mechanism 180 which may be utilized to selectively lock or release the radial position of an intervention device 200 within the receiver 160, such as within the receiver opening 160A. In the embodiments shown in FIGS. 24A, 24B, and 26A-26D, the release mechanism 180 may be hingedly or pivotably adjusted between an opened state and a locked state. However, it should be noted that the intervention device 200 may still be free to move axially when the release mechanism 180 is in the locked state, with the receiver opening 160A functioning as a hole guiding axial movement of the intervention device 200.

FIG. 24A illustrates such a guide member 155C in an opened state such that an intervention device 200 may freely pass through a receiver opening 160A such as a slot. In such an opened state, the guide member 155C may freely traverse along the tracks 151A, 151B.

FIG. 24B illustrates such a guide member 155C in a closed state such that an intervention device 200 may not freely pass through the receiver opening 160A. Additionally, the guide member 155C is locked in place and thus not free to traverse along the tracks 151A, 151B. Such a configuration may improve safety when handling the device.

Figure 25:
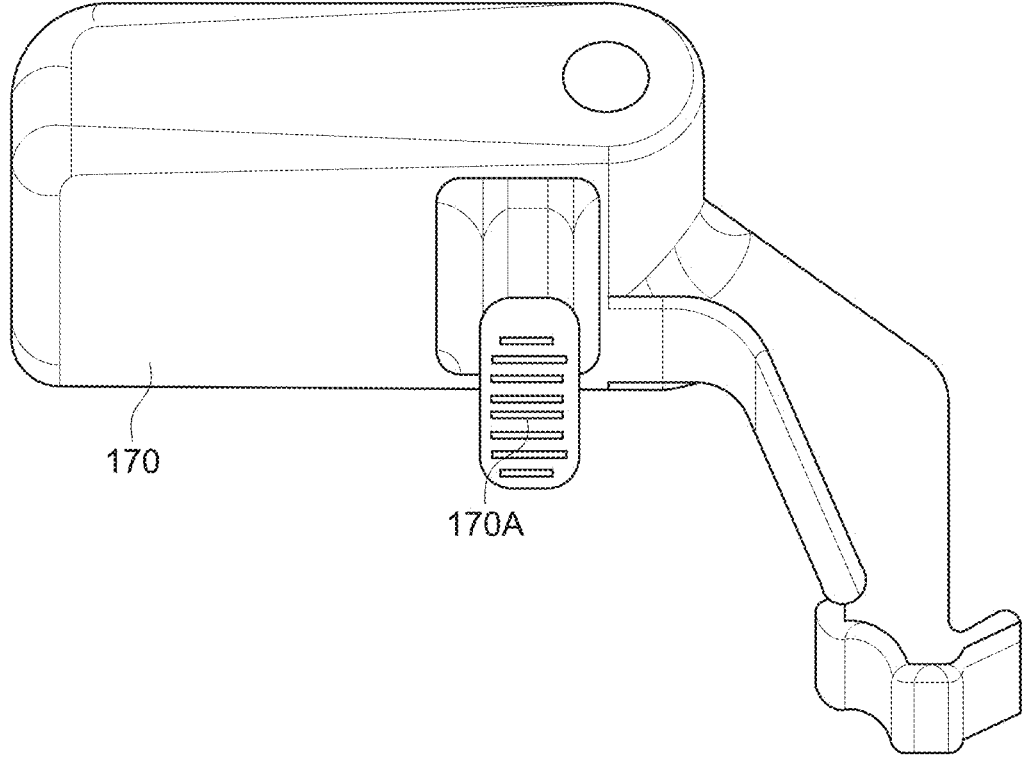
FIG. 25 is a perspective view of a release mechanism of a needle guidance system according to an example embodiment.

FIG. 25 illustrates the bottom of a hinged door, including both the locking mechanism 170 and the release mechanism 180. As shown, the bottom of the release mechanism 170 may include one or more teeth 170A, such as an array of teeth 170A. The teeth 170A may be configured to engage with a rack on the guidance mechanism 150.

Figure 26A:
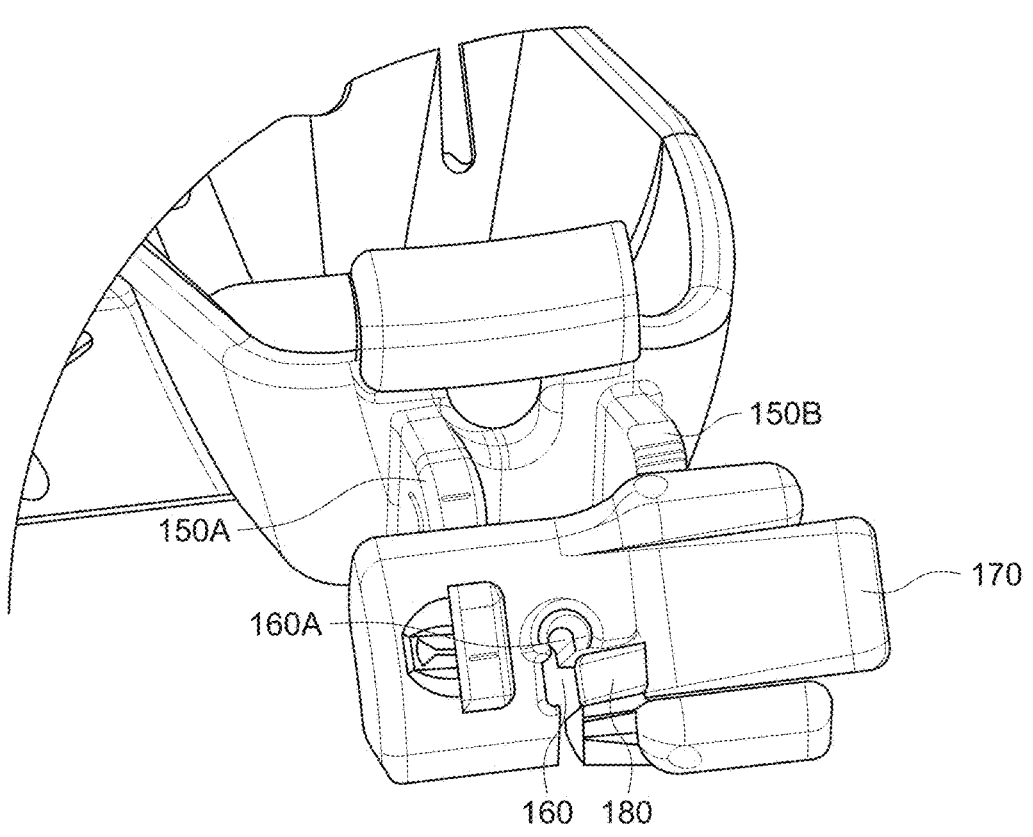
FIG. 26A is a perspective view of a release mechanism of a needle guidance system in a released position according to an example embodiment.
Figure 26B:
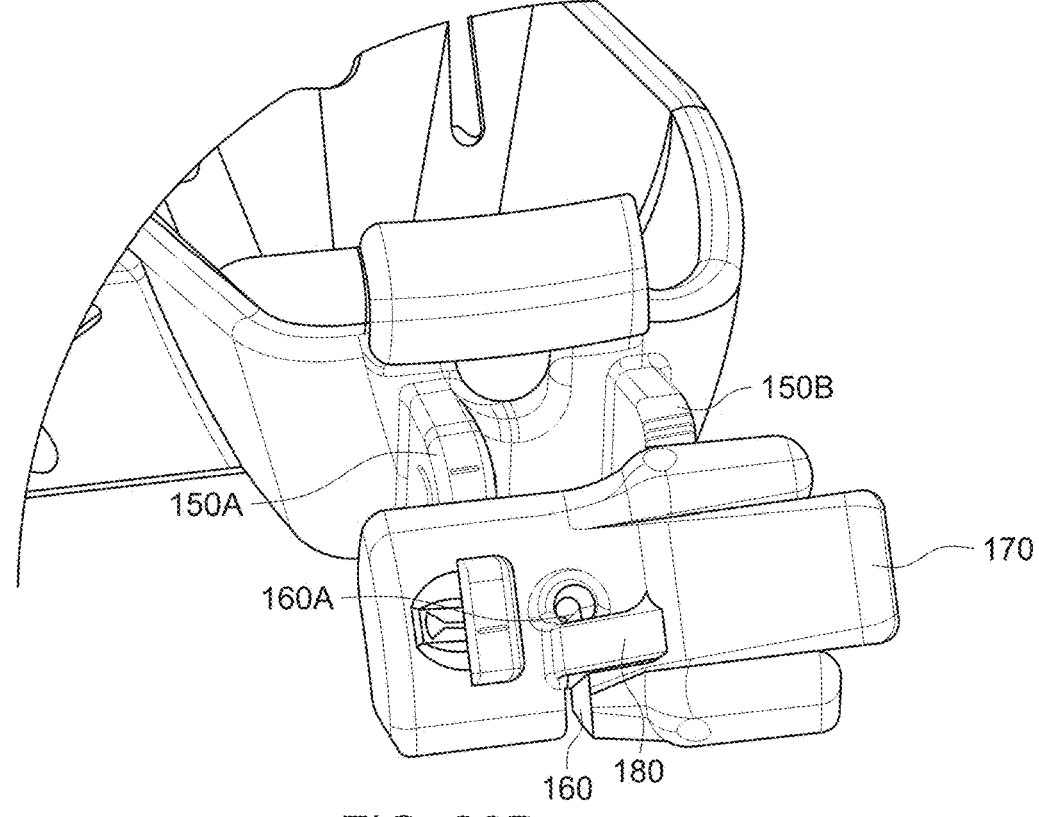
FIG. 26B is a perspective view of a release mechanism of a needle guidance system in a locked position according to an example embodiment.
Figure 26C:
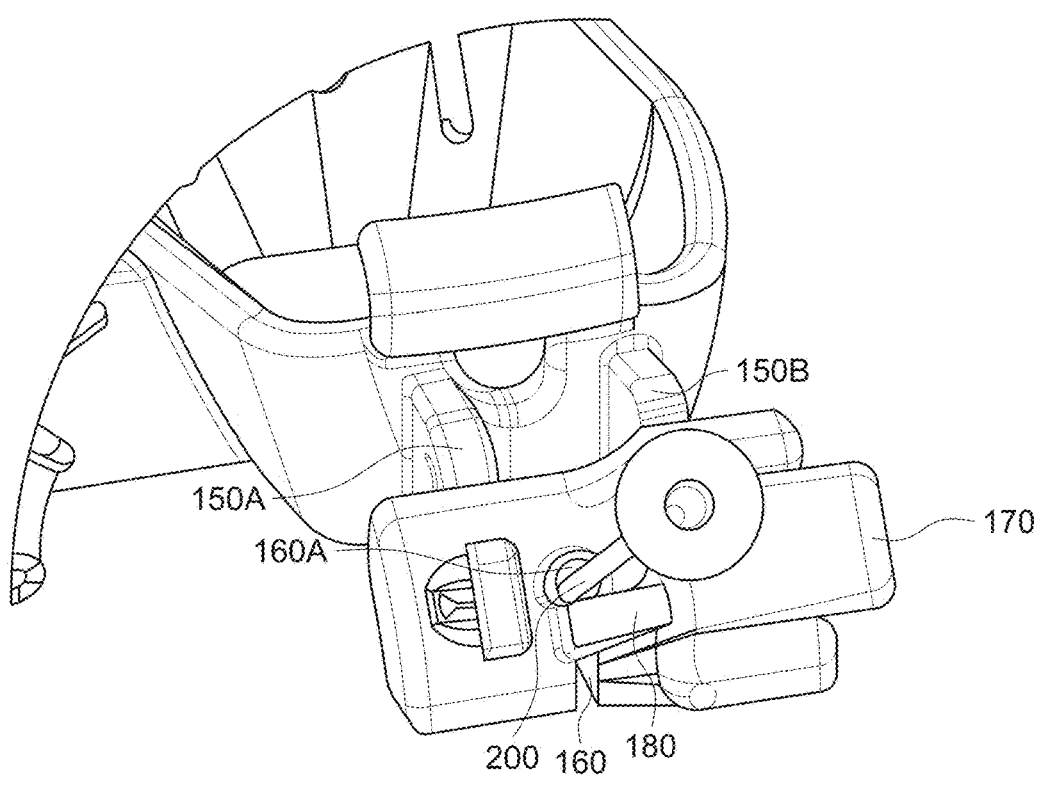
FIG. 26C is a perspective view of a needle inserted within a needle guidance system, with a release mechanism in a locked position, according to an example embodiment.

FIGS. 26A-26D illustrate the guide member 155C and release mechanism 180 in use. FIG. 26A illustrates the guide member 155C being positioned at a desired radial position, with the release mechanism 180 in the opened state. FIG. 26B illustrates the guide member 155C in the desired radial position, with the release mechanism in the closed state. FIG. 26C illustrates an intervention device 200 locked in the desired radial position (but still able to be moved axially), with the locking mechanism 170 similarly being engaged to prevent movement of the guidance mechanism 150. FIG. 26B illustrates the intervention device 200 being released, with the locking mechanism 170 being disengaged and the release mechanism 180 in the opened state.

Figure 26D:
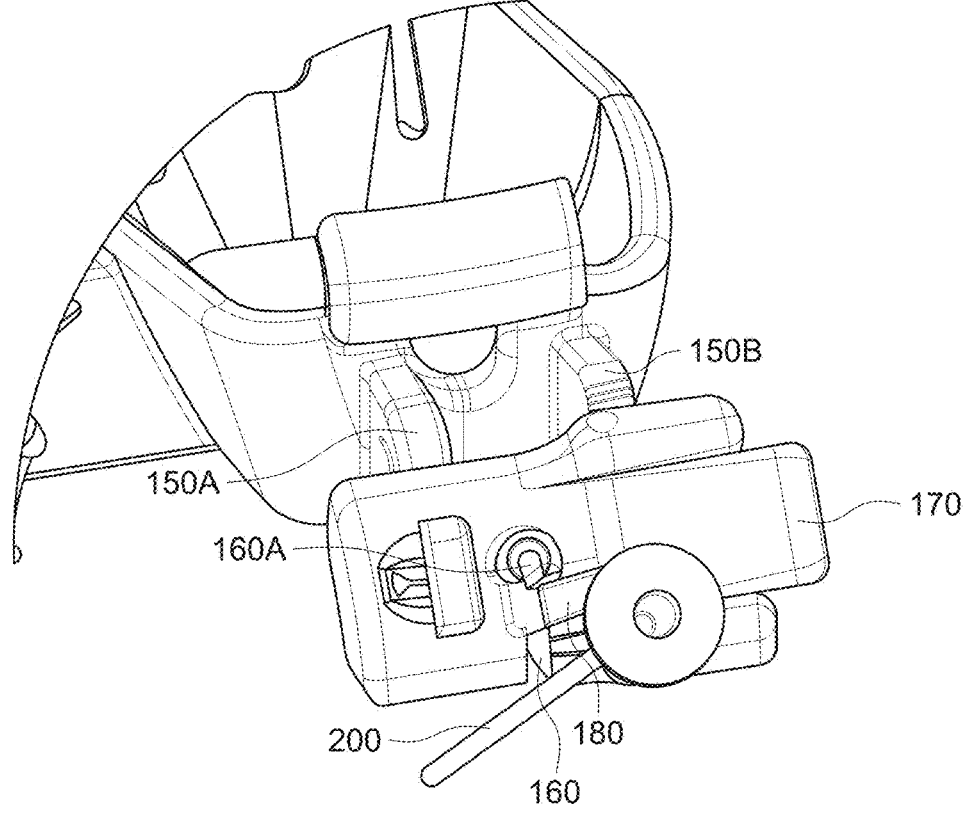
FIG. 26D is a perspective view of a needle released from a needle guidance system, with a release mechanism in a released position, according to an example embodiment.

In use, the depth of a target vessel or location may first be measured with an imaging device 100 such as an ultrasound. The guide member 155C may be configured and adjusted to an appropriate depth setting, with the release mechanism 180 in an opened state as shown in FIG. 26A. The guide member 155C may then be configured to lock the desired depth by adjusting the release mechanism 180 into the locked state as shown in FIG. 26B. The intervention device 200 may then be passed through the receiver opening 160A until it reaches the target location as shown in FIG. 26C. Finally, the release mechanism 180 may be released, and the imaging device 100 and guide member 155C may be lifted away from the intervention device 200 and the patient without disturbing the position and/or angle of the intervention device 200, such as by passing the intervention device 200 through the receiver 160 (e.g., a slot) as shown in FIG. 26D.

As has been previously discussed, the attachment mechanism 110 may be configured to be adaptable to a wide range of imaging devices 100. For example, because different imaging devices 100 may have different sizes, it is desirable to allow the attachment mechanism 110 to be easily adjusted to fit a wide range of sizes. Thus, a universal attachment mechanism 110, capable of being firmly secured over a wide range of imaging devices 100 made by different manufacturers, would prevent the need for operators to purchase or store numerous different types of attachment mechanisms 110.

Figure 27A:
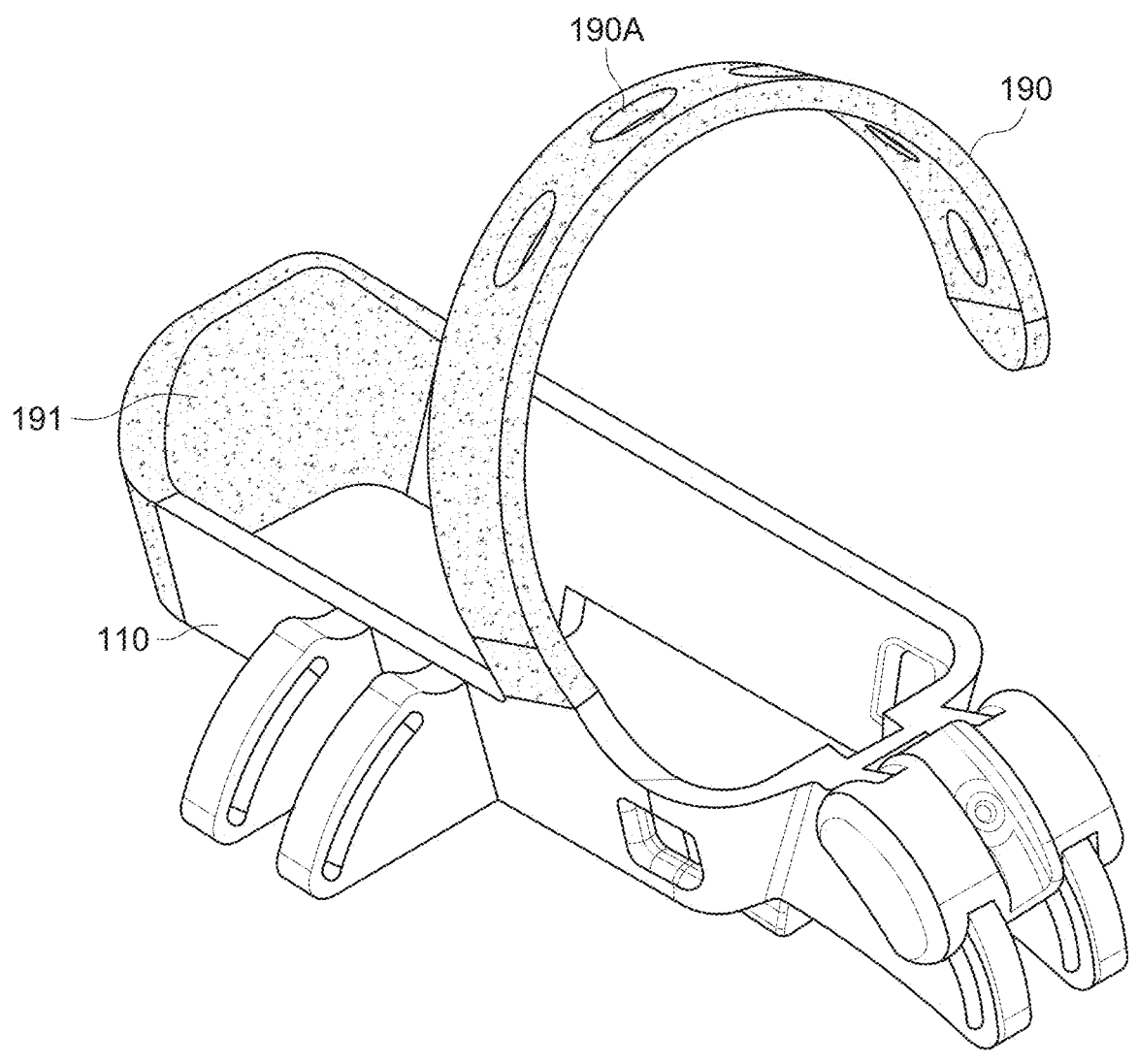
FIG. 27A is a first perspective view of a needle guidance system according to an example embodiment.
Figure 27B:
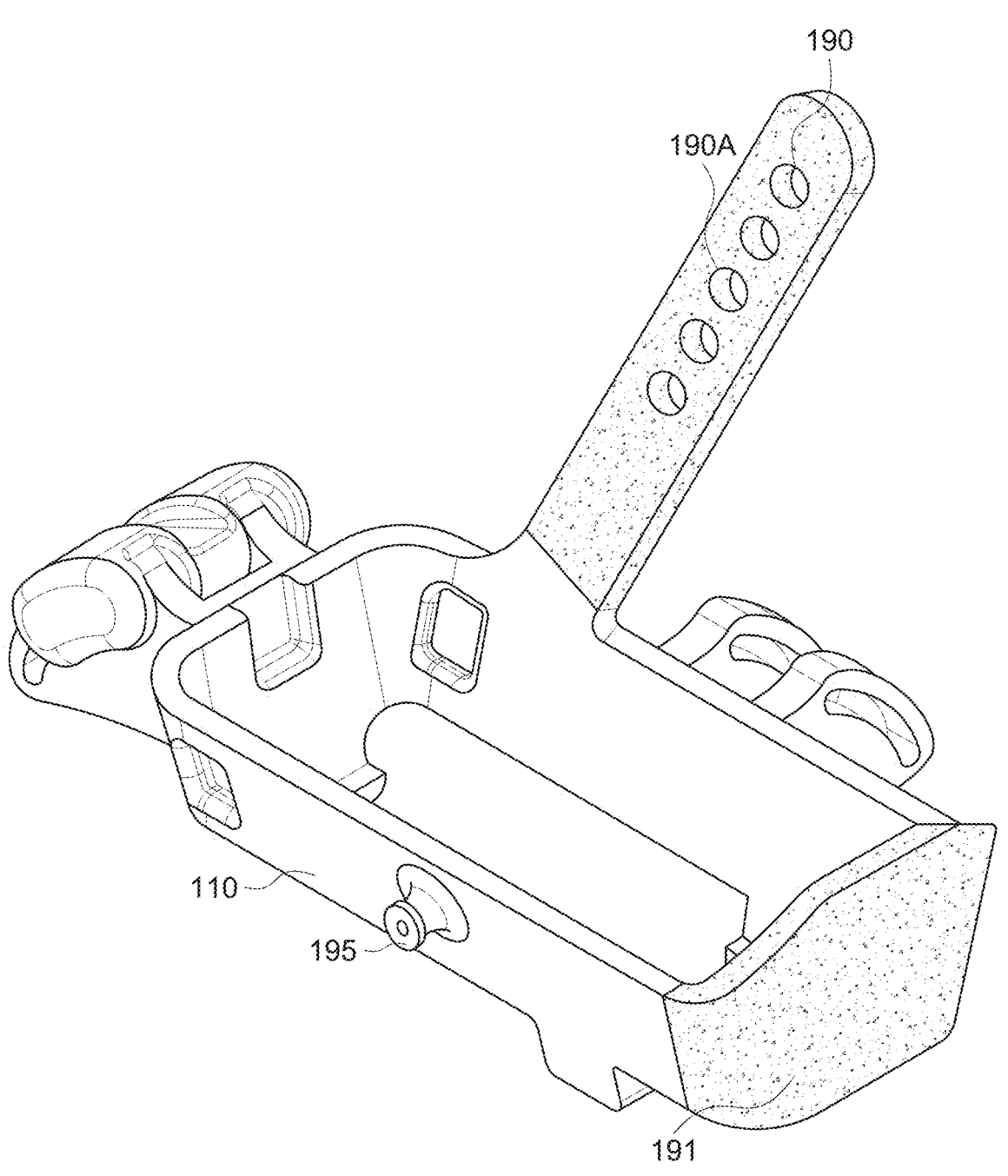
FIG. 27B is a second perspective view of a needle guidance system according to an example embodiment.

FIGS. 27A and 27B illustrate a first example embodiment of an attachment mechanism 110 which may be adaptable to fit over different imaging devices 100 having different sizes. Such an embodiment may include a strap 190 configured to pass over the head of the imaging device 100. The strap 190 may include multiple openings 190A configured to removably engage with a projection 195 on an end or side of the attachment mechanism 110. By selecting which of the openings 190A to secure to the projection 195, the effective length of the strap 190 may be adjusted to fit different imaging devices 100.

In the embodiment shown in FIGS. 27A and 27B, it can be seen that the strap 190 may be fixed to the attachment mechanism 110. More specifically, one end of the strap 190 may be fixed, with the other, opposite end being freely movable so as to allow for securing the strap 190 to the projection 195 via the openings 190A.

Continuing to reference FIGS. 27A and 27B, it should be appreciated that shading represents flexible or semi-flexible materials. The strap 190 is shown as being flexible or semi-flexible to allow it to wrap around the imaging device 100. It can also be seen that a side portion 191 of the attachment mechanism 110 may similarly be comprised of a flexible or semi-flexible material, which allows the attachment mechanism 110 to itself flex to fit different sizes of imaging devices 100. The side portion 191 may alternatively be perforated to enable a greater degree of compliance in some embodiments.

The type of flexible or semi-flexible material may vary in different embodiments and may include, e.g., rubber or various polymeric materials. Additionally, the positioning of the flexible or semi-flexible material may vary from what is shown in FIGS. 27A and 27B. Any portion of the attachment mechanism 110 may be comprised of such a material to allow for flexing. In some embodiments, the entirety of the attachment mechanism 110 may be comprised of such a material, though having rigid portions may aid in structural integrity during operation of the device.

Figure 28A:
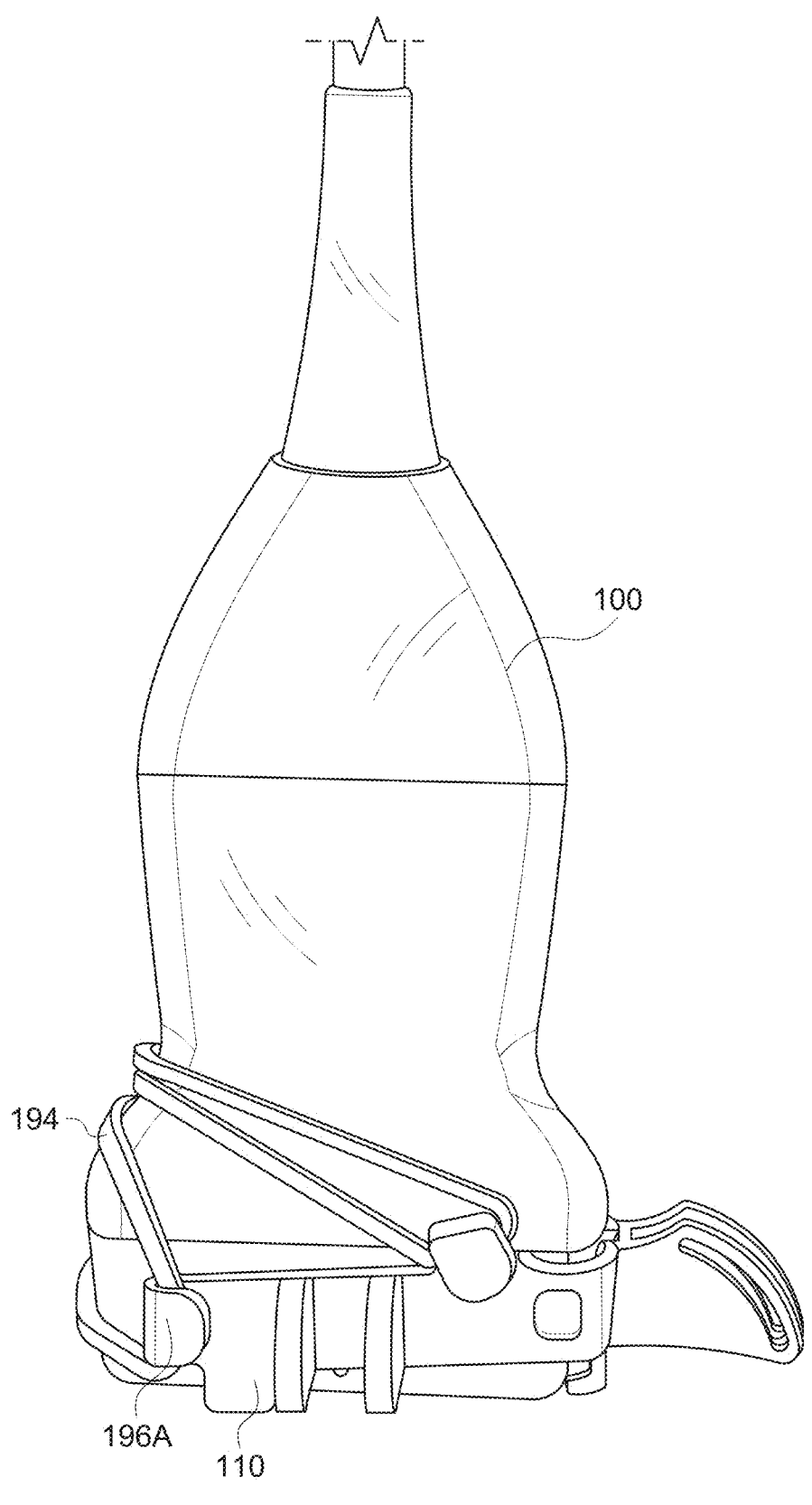
FIG. 28A is a front view of a needle guidance system according to an example embodiment.
Figure 28B:
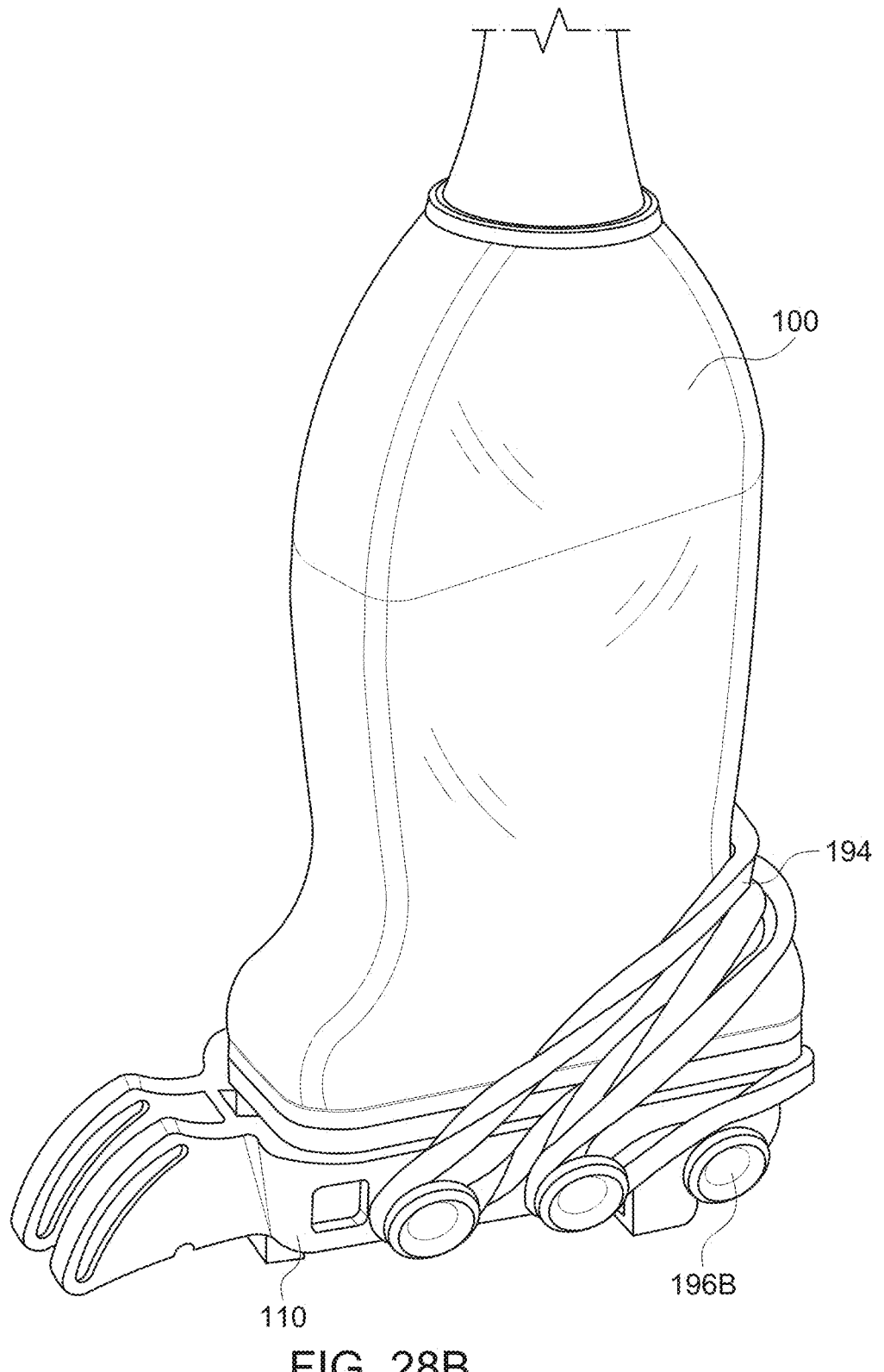
FIG. 28B is a rear perspective view of a needle guidance system according to an example embodiment.

FIGS. 28A and 28B illustrate another embodiment which may be adaptable to fit over a wide range of imaging devices 100. Such an embodiment utilizes one or more bands 194 in place of the strap 190 of the previously discussed embodiment. Both ends or sides of the attachment mechanism 110 may include projections 196A, 196B. The one or more bands 194 may be selected passed over or around the imaging device 200 between the projections 196A, 196B to aid in securing the attachment mechanism 110 to the imaging device 200.

As shown in FIG. 28A, a first end of the attachment mechanism 110 may include first projections 196A comprised of L- or U-shaped brackets to which a first end of one or more bands 194 may be secured. The first projections 196A may be oriented differently such as shown to allow for different angles of attachment. As shown in FIG. 28B, a second end of the attachment mechanism 110 may include second projections 196B comprised of round, flanged projections to which a second end of one or more bands 194 may be secured.

The type, number, size, orientation, and shape of the projections 196A, 196B may vary in different embodiments. Thus, the number of projections 196A, 196B on each portion of the attachment mechanism 110 may differ from what is shown, as more or less projections 196A, 196B may be utilized in different embodiments. Similarly, the positioning of the projections 196A, 196B, such as whether on the ends of the attachment mechanism 110, sides of the attachment mechanism 110, or a combination thereof, may vary.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A guidance system, comprising:
an attachment mechanism configured to be removably attached to an imaging device; and
a guidance mechanism for guiding an intervention device, the guidance mechanism being attached to the attachment mechanism;
wherein the guidance mechanism includes a guide member having an opening and a slot extending from the opening, wherein the intervention device is insertable through the opening of the guide member, wherein the guide member is adjustable along an arcuate path between a plurality of angular positions so as to adjust an angular orientation of the intervention device;
wherein the guide member includes a locking mechanism and a release mechanism comprising a projection extending from the locking mechanism;
wherein, in a locked position, the locking mechanism is in a lowered position and the release mechanism is in a raised position such that (1) movement of the guide member is restricted and (2) the projection of the release mechanism extends perpendicularly across the slot to prevent radial release of the intervention device through the slot; and,
wherein, in an unlocked position, the locking mechanism is in a raised position and the release mechanism is in a lowered position such that (1) the guide member is freely movable and (2) the projection of the release mechanism is pivoted downwardly so as to expose the slot to allow radial release of the intervention device through the slot.

2. The guidance system of claim 1, wherein a width of the locking mechanism is greater than a width of the release mechanism.

3. The guidance system of claim 1, wherein the opening is comprised of a C-shaped opening.

4. The guidance system of claim 1, wherein the slot is perpendicular to a longitudinal axis of the guide member.

5. The guidance system of claim 1, wherein the guidance mechanism is fixedly attached to the attachment mechanism.

6. The guidance system of claim 1, wherein the guidance mechanism is fixedly attached to a first side of the attachment mechanism.

7. The guidance system of claim 6, further comprising a second guidance mechanism fixedly attached to a first end of the attachment mechanism.

8. The guidance system of claim 7, wherein the first guidance mechanism is at a right angle with respect to the second guidance mechanism.

9. The guidance system of claim 7, wherein the first guidance mechanism and the second guidance mechanism are both affixed simultaneously to the attachment mechanism.

10. The guidance system of claim 1, wherein the release mechanism is comprised of a hinged member.

11. The guidance system of claim 1, wherein the attachment mechanism includes at least one tab for releasably engaging with the imaging device.

12. The guidance system of claim 11, wherein the at least one tab includes a curved inner surface for engaging with a curved outer surface of the imaging device.

13. The guidance system of claim 1, wherein the attachment mechanism is configured to adapt to a plurality of imaging devices, each of the plurality of imaging devices having a different size.

14. The guidance system of claim 1, wherein the attachment mechanism comprises a portion composed of a flexible material such that the attachment mechanism flexes to fit different types of imaging devices.

15. A guidance system, comprising:

an attachment mechanism configured to be removably attached to an imaging device; and a first guidance mechanism for guiding an intervention device, the first guidance mechanism being attached to a first side of the attachment mechanism;

a second guidance mechanism for guiding the intervention device, the second guidance mechanism being attached to a first end of the attachment mechanism such that the first guidance mechanism is at a right angle with respect to the second guidance mechanism;

wherein each of the first guidance mechanism and the second guidance mechanism includes a guide member having opening and a slot extending from the opening, wherein the slot is perpendicular to a longitudinal axis of the guide member, wherein the intervention device is insertable through the opening of the guide member, wherein the guide member of each of the first guidance mechanism and the second guidance mechanism is adjustable along an arcuate path between a plurality of angular positions so as to adjust an angular orientation of the intervention device; and, wherein the guide member of each of the first guidance mechanism and the second guidance mechanism includes a locking mechanism and a release mechanism extending from the locking mechanism;

wherein, in a locked position, the locking mechanism is in a lowered position and the release mechanism is in a raised position such that (1) movement of the guide member is restricted and (2) the release mechanism extends perpendicularly across the slot to prevent radial release of the intervention device through the slot; and, wherein, in an unlocked position, the locking mechanism is in a raised position and the release mechanism is in a lowered position such that (1) the guide member is freely movable and (2) the release mechanism is pivoted downwardly so as to expose the slot to allow radial release of the intervention device through the slot.

16. The guidance system of claim 15, wherein the opening is comprised of a C-shaped opening.

17. The guidance system of claim 15, wherein the release mechanism is comprised of a projection.

18. The guidance system of claim 15, wherein a width of the locking mechanism is greater than a width of the release mechanism.

19. The guidance system of claim 15, wherein the first guidance mechanism and the second guidance mechanism are each fixedly attached to the attachment device.

20. The guidance system of claim 15, wherein the first guidance mechanism and the second guidance mechanism are both simultaneously affixed to the attachment mechanism.

\* \* \* \* \*